(12) United States Patent
Li

(10) Patent No.: US 10,011,638 B2
(45) Date of Patent: Jul. 3, 2018

(54) PTEN ANTAGONIST PEPTIDES AND METHODS OF USING THE SAME

(71) Applicant: SHRINERS HOSPITALS FOR CHILDREN, Tampa, FL (US)

(72) Inventor: Shuxin Li, Wynnewood, PA (US)

(73) Assignee: Shriners Hospitals for Children, Tampa, FL (US)

( * ) Notice: Subject to any disclaimer, the term of this patent is extended or adjusted under 35 U.S.C. 154(b) by 0 days.

(21) Appl. No.: 15/204,695

(22) Filed: Jul. 7, 2016

(65) Prior Publication Data

US 2016/0311857 A1   Oct. 27, 2016

Related U.S. Application Data

(63) Continuation of application No. PCT/US2015/010597, filed on Jan. 8, 2015.

(60) Provisional application No. 61/925,016, filed on Jan. 8, 2014.

(51) Int. Cl.
*C07K 7/08* (2006.01)
*A61K 47/64* (2017.01)
*A61K 38/00* (2006.01)

(52) U.S. Cl.
CPC .............. *C07K 7/08* (2013.01); *A61K 47/645* (2017.08); *A61K 38/00* (2013.01)

(58) Field of Classification Search
None
See application file for complete search history.

(56) References Cited

U.S. PATENT DOCUMENTS

2008/0234183 A1   9/2008   Hallbrink et al.
2012/0039861 A1   2/2012   Parsons

FOREIGN PATENT DOCUMENTS

WO   WO 2011/044701 A1   4/2011
WO   WO 2013/106909 A1   7/2013

OTHER PUBLICATIONS

Zhang et al., Critical Role of Increased PTEN Nuclear Translocation in Excitotoxic and Ischemic Neuronal Injuries, May 1, 2013, The Journal of Neuroscience 33(18):7997-8008.*

(Continued)

*Primary Examiner* — John D Ulm
(74) *Attorney, Agent, or Firm* — Baker Botts LLP

(57) ABSTRACT

The presently disclosed subject matter relates to antagonists of PTEN and methods of using the same. In particular, the presently disclosed subject matter provides for PTEN antagonist peptides for use in treating central nervous system disorders. In an exemplary embodiment, the presently disclosed subject matter provides methods for promoting nerve fiber growth in a subject by administering to the subject a therapeutically effective amount of a PTEN antagonist peptide.

5 Claims, 12 Drawing Sheets

(56) References Cited

OTHER PUBLICATIONS

Ohtake et al., The effect of systemic PTEN antagonist peptides on axon growth and functional recovery after spinal cord injury, May 2014, Biomaterials 35(16): 4610-4626.*
Amiri et al., "Pten deletion in Adult Hippocampal Neural Stem/Progenitor Cells Causes Cellular Abnormalities and Alters Neurogenesis," J Neurosci 32(17):5880-5890 (2012).
Bolduc et al., "Phosphorylation-mediated PTEN conformational closure and deactivation revealed with protein semisynthesis," eLife 2: e00691, pp. 1-19 (2013).
Christie et al., "PTEN Inhibition to Facilitate Intrinsic Regenerative Outgrowth of Adult Peripheral Axons," *J Neurosci* 30(27):9306-9315 (2010).
Goebbels et al., "Elevated Phosphatidylinositol 3,4,5-Trisphosphate in Glia Triggers Cell-Autonomous Membrane Wrapping and Myelination," *J Neurosci* 30(26):8953-8964 (2010).
Groszer et al., "Negative Regulation of Neural Stem/Progenitor Cell Proliferation by the Pten Tumor Suppressor Gene in Vivo," Science 294:2186-2189 (2001).
International Search Report and Written Opinion dated May 6, 2015 in International Application No. PCT/US2015/010597.
Liu et al., "PTEN deletion enhances the regenerative ability of adult corticospinal neurons," Nature Neurosci 13(9):1075-1081 (2010).
Lobo et al., "Germline and somatic cancer-associated mutations in the ATP-binding motifs of PTEN influence its subcellular localization and tumor suppressive function," Hum Mol Genet 18(15):2851-2862 (2009).
Nakashima et al., "Small Molecule Protein Tyrosine Phosphatase Inhibition as a Neuroprotective Treatment after Spinal Cord Injury in Adult Rats," J Neurosci 28(29):7293-7303 (2008).
Ning et al., "PTEN depletion rescues axonal growth defect and improves survival in SMN-deficient motor neurons," Hum Mol Genet 19(16):3159-3168 (2010).
Park et al., "Promoting Axon Regeneration in the Adult CNS by Modulation of the PTEN/mTOR Pathway," Science 322:963-966 (2008).
Park et al., "PTEN/mTOR and axon regeneration," *Exp Neurol* 223:45-50 (2010).
Rapoport et al., "TAT-based drug delivery system—new directions in protein delivery for new hopes?" Expert Opin on Drug Deliv 6(5):453-463 (2009).
Schwarze et al., "In Vivo Protein Transduction: Delivery of a Biologically Active Protein into the Mouse," Science 285:1569-1572 (1999).
Sun et al., "Sustained axon regeneration induced by co-deletion of PTEN and SOCS3," *Nature* 480:372-375 (2011).
Valiente et al., "Binding of PTEN to Specific PDZ Domains Contributes to PTEN Protein Stability and Phosphorylation by Microtubule-associated Serine/Threonine Kinases," J Biol Chem 280(32):28936-28943 (2005).
Walker et al., "Systemic Bisperoxovanadium Activates Akt/mTOR, Reduces Autophagy, and Enhances Recovery following Cervical Spinal Cord Injury," PLoS One 7(1):e30012 (2012).

* cited by examiner

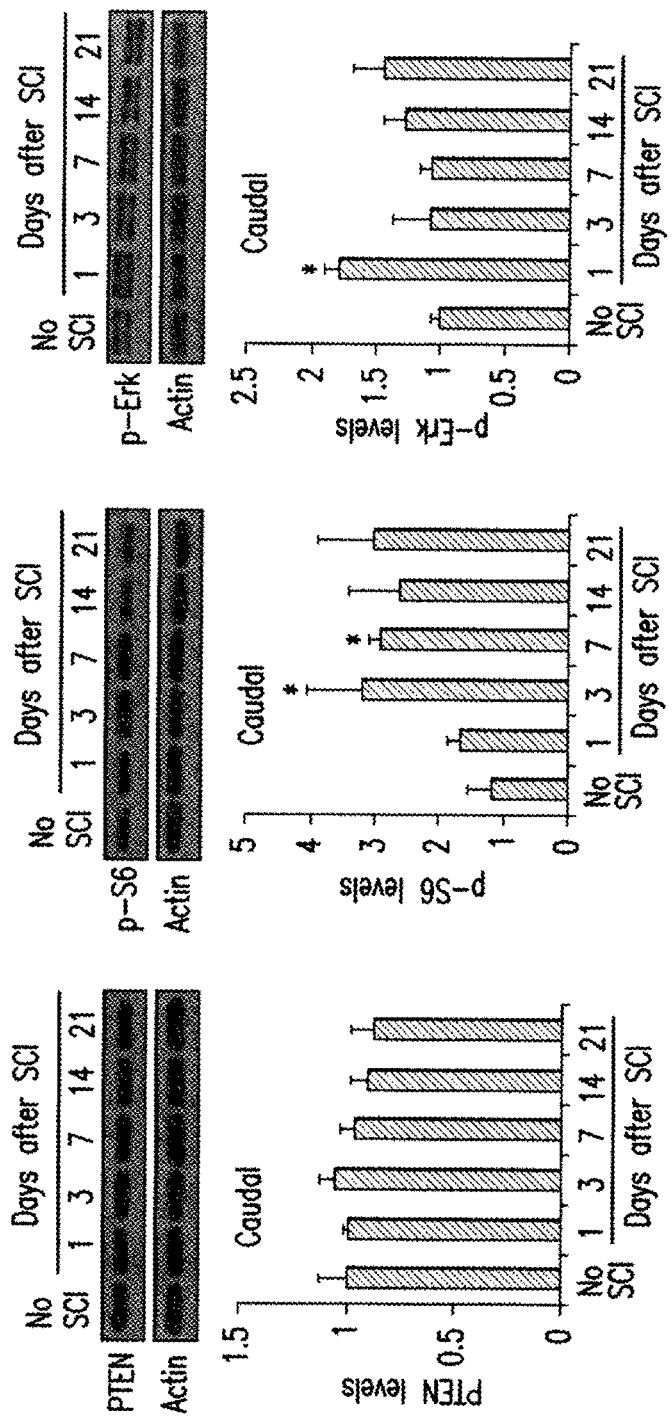

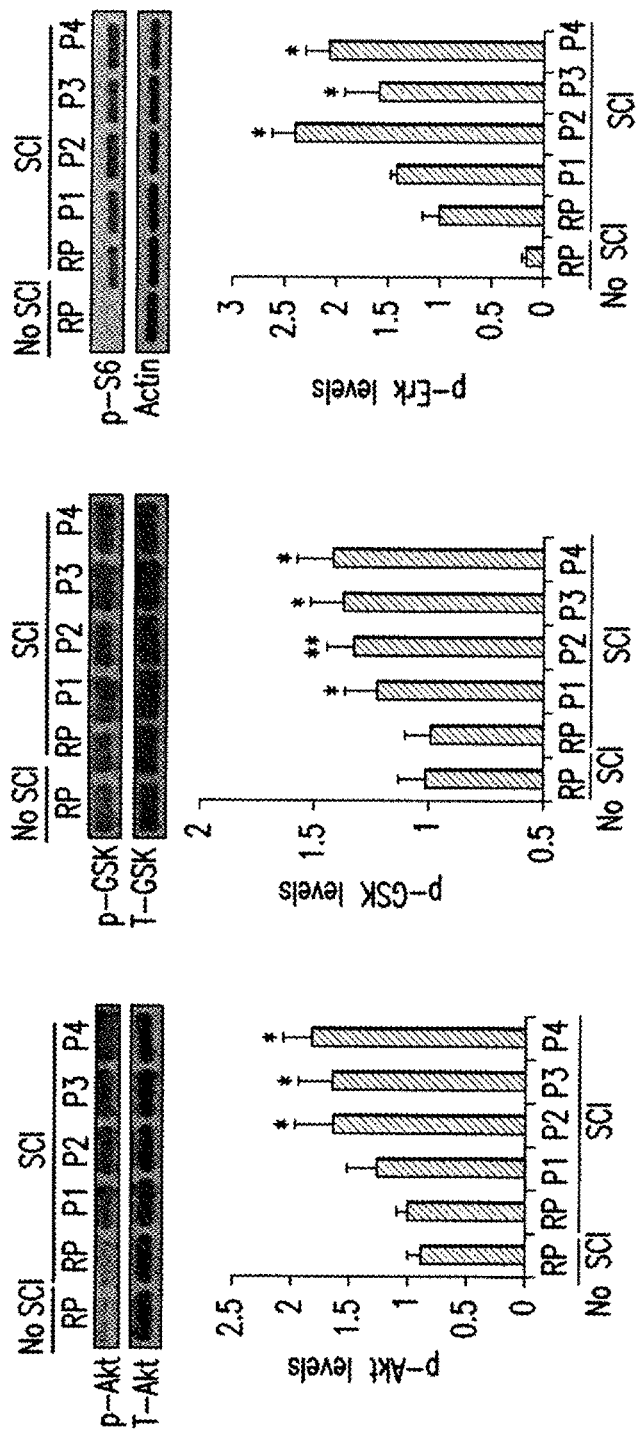

PTEN ANTAGONIST PEPTIDES AND METHODS OF USING THE SAME

PRIORITY CLAIM

This application is a continuation of International Patent Application No. PCT/US2015/010597, filed Jan. 8, 2015, which claims priority to U.S. Provisional Application Ser. No. 61/925,016, filed Jan. 8, 2014, priority to each of which is claimed, and the contents of each of which are incorporated by reference in their entireties herein.

GRANT INFORMATION

This invention was made with government support under Grant No. 1R21NS066114 awarded by National Institute of Health. The government has certain rights in the invention.

SEQUENCE LISTING

The specification further incorporates by reference the Sequence Listing submitted via EFS on Jan. 8, 2015. Pursuant to 37 C.F.R. § 1.52(e)(5), the Sequence Listing text file, identified as 006910_6016CONSL.txt, is 1,572 bytes in size and was created on Jul. 8, 2016. The Sequence Listing, electronically filed on Jul. 8, 2016, does not extend beyond the scope of the specification and thus does not contain new matter.

BACKGROUND

Axonal disconnection in the central nervous system (CNS) can result in persistent deficits in many neurological disorders, such as spinal cord injury (SCI), because axons in the mammalian CNS do not regenerate. Failure of axon regeneration in CNS is believed to be due to both a non-permissive environment, including myelin-associated growth inhibitors (3, 4), scar-sourced chondroitin sulfate proteoglycans (5, 6), repulsive axon guidance cues (7, 8) and lack of neurotraphic factors (9-11), and the reduced intrinsic growth capacity of mature neurons (12). Several cell autonomous molecules, including cAMP, RhoA, Kruppel-like factors, mammalian target of rapamycin (mTOR) and phosphatase and tensin homolg (PTEN), have been reported to play roles in determining neuronal growth ability (13-16). PTEN appears to be particularly important for controlling the regenerative capacity of injured axons (2).

Conditional deletion of PTEN, a negative regulator of mTOR, has been shown to enhance axon growth after SCI or optic nerve injury and protect retinal ganglion cells (RGCs) from death following axotomy (14, 16, 17). The axon growth-promoting action of PTEN deletion is reduced by the mTOR inhibitor rapamycin. Deletion of tuberous sclerosis complex 1 (TSCI), a negative regulator of mTOR, also activated mTOR and enhanced axon regeneration by principally mimicking the effect of PTEN deficiency. PTEN deletion or inhibition has been reported to stimulate axon growth of several neuronal populations, including RGCs, dorsal root ganglion (DRG) sensory neurons, corticospinal tract (CST) and other motor neurons (2, 14, 16, 18, 19). In addition, PTEN blockade with general phosphatase inhibitor bisperoxovanadium (bpV) protected spinal cord tissues after SCI (20, 21). Application of bpV may block PTEN function (18) but bpV compounds also target other enzymes and may cause clinical side effects. Therefore, there remains a need for efficient and selective reduction of PTEN activity.

SUMMARY

The presently disclosed subject matter relates to antagonists of PTEN and methods of using the same. In particular, the presently disclosed subject matter provides for PTEN antagonist peptides for use in treating central nervous system disorders.

In certain embodiments, the present subject matter provides a method for promoting nerve fiber growth in a subject, e.g., a human, by administering to the subject a therapeutically effective amount of a PTEN antagonist peptide. In certain embodiments, one or more PTEN antagonist peptides are administered to a subject.

In certain embodiments, the disclosure provides methods for treating a central nervous system disorder by administering a pharmaceutical composition including a therapeutically effective amount of a PTEN antagonist peptide to a subject. In certain embodiments, the central nervous system disorder can include a spinal cord injury, a stroke, multiple sclerosis, an optic nerve injury, an optic nerve disorder or a traumatic brain injury.

In certain embodiments, the present disclosure provides for PTEN antagonist peptides. In certain embodiments, the PTEN antagonist peptides include peptides having an amino acid sequence of SEQ ID NO:1, SEQ ID NO:2, SEQ ID NO:3, SEQ ID NO:4 or SEQ ID NO: 5. The presently disclosed subject matter further provides for pharmaceutical compositions which include a therapeutically effective amount of a PTEN antagonist peptide.

BRIEF DESCRIPTION OF THE FIGURES

FIG. 3A-I. Traumatic injury altered PTEN expression and increased S6 and Erk activity in the lesioned spinal cord. The levels of PTEN (A, D, G), p-S6 (active form, B, E, H) and p-Erk (active form, C, F, I) were analyzed with Western blots from tissue lysates of fresh spinal cord blocks 2-6 mm rostral to lesion (A, B, C), at lesion site (2 mm rostral to and caudal to injury center, containing the lesion, D, E, F), 2-6 mm caudal to the lesion (G, H, I), or from the same level of spinal cord in no-SCI controls. Actin was also detected in the same blots (bottom bands). Bar graphs below the bands indicate densitometric analysis of PTEN, p-S6 and p-Erk from multiple animals. Trauma significantly increased PTEN levels rostral to the lesion although there was a slight reduction at the lesion site. SCI also significantly enhanced levels of p-S6 and p-Erk several days after lesion. Means±SEM were shown, n=3 from 3 mice in each group, *p<0.05 compared to the no-SCI controls.

FIG. 4A-C. PAPs 1-4 enhance Akt and S6 activity and suppress GSK-3β activity in lesioned spinal cord. Western blots indicate the levels of phosphorylated Akt (p-Akt, active form, A), GSK-3β (p-GSK, inactive form, B) and S-6 (p-861, C) in the supernatants of fresh spinal cord tissues 2 mm rostral to and 2 mm caudal to dorsal transection 48 hrs after lesion at T7 (or the same level of spinal cord in no-SCI controls). Although the total protein levels (t-Akt, t-GSK or actin) were similar in the supernatants, treatments with PAPs 1-4 significantly increased the levels of p-Art, p-GSK and p-S6. Bar graphs below the bands indicate densitometric analysis of p-Akt, p-GSK d p-S6 levels in the lesioned spinal cord (n=4 mice per group). P1: PAP1; P2; PAP2; P3; PAP3; started here P4; PAP4. Total Akt, GSK-3β or actin were detected from the same tissue samples via immunoblotting (bottom bands). Treatment with PAPs 1-4 enhanced the levels of p-Akt, p-GSK and p-S6. Means±SEM were shown and the differences indicated were compared to RP-treated SCI controls. *<0.05, **<0.01.

DETAILED DESCRIPTION

Figure 1A:
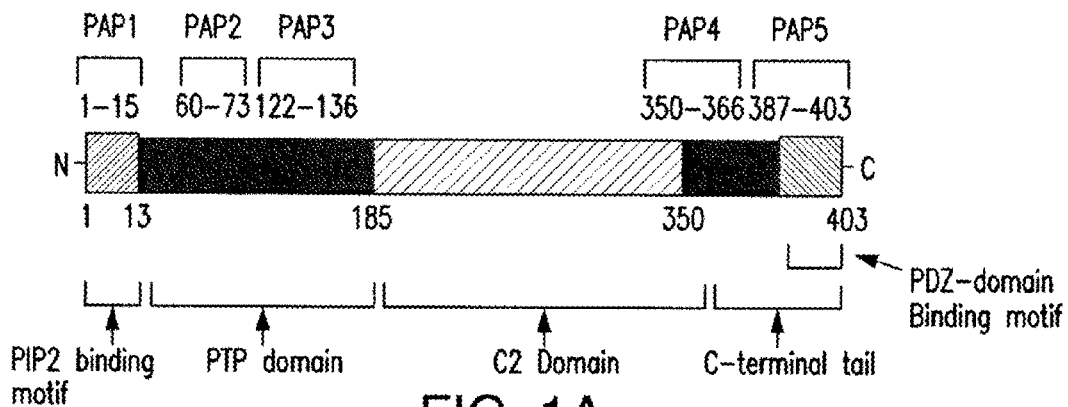
FIG. 1A-E. PAPs 1-4 increased neurite outgrowth of DRG neurons and CGNs cultured on purified CNS myelin. A, Schematic indicates the targeting sequence of PAPs 1-5 and the targeted functional domains of PTEN. B, Adult DRG neurons were cultured for 5 days on coverslips spotted with CNS myelin in the center area and stained with Tuj1. Very few neurites were detected on myelin spots in cultures treated with DMSO or RP. However, a greater number of neurites were detected on myelin spots in cultures treated with PAPs 1-4, but not PAP5. At high magnification (right images), a number of clustered neurites (red) were seen on myelin spots in PAPs 1-4-treated neurons. Scale bars: 200 μm in left images, 50 μm in right images. C, High level of PTEN protein was detected in the bodies and neurites of cultured DRGs and was co-localized with neuronal marker Tuj1. D, Quantification indicates longer axon length of DRG neurons treated with PAPs 1-4, but not PAP5, on myelin spots. The numbers indicate means±SEM from 6-0 myelin spots per group. The differences indicated were compared to RP-treated controls. E, Dissociated CGNs cultured from postnatal day 7 mice were treated with vehicle DMSO or PAPs 1-5 in the absence or presence CNS myelin (Mye, 50 μg/ml). Neurite outgrowth per CGN was manually traced and quantified 24 hrs after cell plating using NIH and Photoshop software. The numbers in bar graphs indicate means±SEM from 3-5 experiments. The differences indicated are compared to vehicle controls. Treatment with PAPs 1-4, but not with PAP5, significantly increased neurite length of CGNs cultured on CNS myelin. In D and E, **$p<0.01$, Student's t-test.

The presently disclosed subject matter relates to PTEN antagonist peptides and methods of their use. For example, in certain embodiments, the present disclosed subject matter provides for PTEN antagonist peptides for use in treating central nervous system disorders and promoting nerve fiber regeneration and/or growth in a subject.

As disclosed herein, the administration of PTEN antagonist peptides in mouse models of spinal injuries promotes central nervous system nerve fiber regeneration and enhanced recovery of locomotor function. Accordingly, inhibition of PTEN in the central nervous system via the compositions and methods described herein can be used to promote nerve fiber growth and treat central nervous system disorders, e.g., spinal cord injuries.

In certain embodiments, the present disclosure provides methods of treating a central nervous system disorder, where the method includes treating a patient in need with a therapeutically effective amount of a PTEN antagonist peptide. The present disclosure also provides for promoting axon growth or regeneration in a patient in need of such treatment, the method of which includes treating the patient with a therapeutically effective amount of a PTEN antagonist peptide.

An "individual," "patient" or "subject," as used interchangeably herein, can be a human or non-human animal. Non-limiting examples of non-human animal subjects include non-human primates, dogs, cats, mice, rats, guinea pigs, rabbits, pigs, fowl, horses, cows, goats, sheep and cetaceans.

PTEN Antagonist Peptides

In certain embodiments, the presently disclosed subject matter is directed to the use of peptides capable of antagonizing PTEN function. In certain embodiments, the PTEN antagonist peptides of the present disclosure target the active regions of PTEN to selectively inhibit or reduce PTEN activity.

A "peptide", as used herein, can be a single linear polymer chain of amino acids bonded together by peptide bonds, with the first amino acid being at the amino (N) terminus and the last amino acid being at the carboxyl (C) terminus. The term also includes modifications of such a peptide, including, but not limited to, pegylation, glycosylation, acetylation and phosphorylation. In addition, protein fragments, analogs, mutated or variant proteins and fusion proteins are included within the meaning of the term, and further includes molecules in which one or more amino acid analogs or non-canonical or unnatural amino acids are incorporated.

A "peptide antagonist" to PTEN, as used herein, refers to a peptide that blocks, downregulates, suppresses or otherwise reduces PTEN biological activity. The term "antagonist" does not imply a specific mechanism of biological action and is deemed to expressly include and encompass all possible pharmacological, physiological and biochemical interactions with PTEN, whether direct or indirect, or through another mechanism. In certain embodiments, a PTEN antagonist peptide can bind to PTEN. Antagonist activity can be detected by known in vitro methods or in vivo functional assay methods. An antagonist can also include a compound that decreases the interaction of PTEN with another molecule, such as a downstream target of PTEN (e.g., Akt).

The term "PTEN antagonist peptide" is intended to encompass peptides comprising the exemplary amino acid sequence of MTAIIKEIVSRNKRR (SEQ ID NO:1). PTEN antagonist peptides also encompass peptides comprising an amino acid sequence selected from the group consisting of: KHKNHYKIYNLCAE (SEQ ID NO:2), IHCKAGKGRTGVMIC (SEQ ID NO:3), TVEEPSNPEASSSTSVTPD (SEQ ID NO:4), and PENEPFDEDQHSQITKV (SEQ ID NO:5), as well as fragments thereof (e.g., functional fragments thereof) and variants thereof (e.g., functional variants thereof). In certain embodiments, the presently disclosed subject matter provides for the use of an isolated or purified PTEN antagonist peptide and variants and fragments thereof. Variants also include peptides that are substantially homologous to the PTEN antagonist peptide.

As used herein, two peptides (or regions thereof) are substantially homologous when the amino acid sequences are at least about 60-65%, 65-70%, 70-75%, 80-85%, 90-95% or 95-99% or more homologous. In certain embodiments, two peptides (or regions thereof) are substantially homologous when the amino acid sequences are at least about 90-95% or more homologous.

In certain embodiments, the presently disclosed subject matter further provides for derivatives of PTEN antagonist peptides. A derivative of a PTEN antagonist peptide is a peptide in which one or more physical, chemical or biological properties have been altered. Such modifications include, but are not limited to, amino acid substitutions, modifications, additions or deletions, alterations in the pattern of lipidation, glycosylation or phosphorylation, reactions of free amino, carboxyl or hydroxyl side groups of the amino acid residues present in the peptide with other organic and non-organic molecules and other modifications, without substantially altering the PTEN antagonist function of the peptide.

It is generally recognized that conservative amino acid changes are least likely to perturb the structure and/or function of a peptide. Accordingly, in certain embodiments, the presently disclosed subject matter encompasses one or more conservative amino acid changes within a PTEN antagonist peptide. Conservative amino acid changes generally involve substitution of one amino acid with another that is similar in structure and/or function (e.g., amino acids with side chains similar in size, charge and shape). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, in certain embodiments, one or more amino acid residues within a PTEN antagonist peptide can be replaced with other amino acid residues from the same side chain family and the altered protein can be tested for retained PTEN antagonist function. PTEN antagonist activity can be determined using techniques known in the art. For example, PTEN antagonist activity can be determined by looking at a wild type PTEN activity and comparing the inhibition or reduction of such activity when the antagonist polypeptide is used.

In certain embodiments, the presently disclosed subject matter also provides for fusion peptides including PTEN antagonist peptides. The term "fusion" refers to joining of different peptide or protein segments by genetic or chemical methods wherein the joined ends of the peptide or protein segments can be directly adjacent to each other or can be separated by linker or spacer moieties such as amino acid residues or other linking groups. In certain embodiments, the peptide sequence can further include a cell-penetrating sequence, such as a transactivator of transcription (TAT) sequence at the C-terminus. In certain embodiments, the TAT sequence can have the following amino acid sequence GRKKRRQRRRC (SEQ ID NO:6). TAT-fusion proteins retain their biological activity and are able to rapidly and efficiently access the intracellular space of cultured cells and intact tissues following extracellular application in vitro and in vivo (24).

In certain embodiments, the PTEN antagonist peptide of the present disclosure can be obtained using recombinant DNA- and/or RNA-mediated protein expression techniques, or any other methods of preparing peptides or, when applicable, fusion proteins. Modifications can be introduced into the PTEN antagonist peptide of the present disclosure by standard techniques known in the art, such as site-directed mutagenesis and PCR-mediated mutagenesis, provided that activity, e.g., binding activity, is retained.

Pharmaceutical Compositions

In certain embodiments, the presently disclosed subject matter provides for pharmaceutical compositions which include one or more PTEN antagonist peptides or functional fragment thereof. The presently disclosed subject matter further provides pharmaceutical compositions which include a PTEN antagonist peptide that can be administered in any sterile, biocompatible pharmaceutical carrier, including, but not limited to, saline, buffered saline, dextrose and water. In certain embodiments, the composition can be in a liquid or lyophilized form and comprises a diluent (e.g., Tris, citrate, acetate or phosphate buffers) having various pH values and ionic strengths, solubilizer such as TWEEN™ or Polysorbate, carriers such as human serum albumin or gelatin, preservatives such as thimerosal, parabens, benzylalconium chloride or benzyl alcohol, antioxidants such as ascrobic acid or sodium metabisulfite and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

In certain embodiments, PTEN antagonist peptides can be administered to the patient intravenously and/or subcutaneously in a pharmaceutically acceptable carrier such as physiological saline. In certain embodiments, the carrier can be a solvent or dispersion medium containing, for example, water, ethanol, polyol (for example, glycerol, propylene glycol, and liquid polyethylene glycol, and the like), and suitable mixtures thereof. Standard methods for intracellular delivery of peptides can be used (e.g., delivery via liposome). Such methods are well known to those of ordinary skill in the art. The formulations of this presently disclosed subject matter are useful for parenteral administration, such as intravenous, subcutaneous, intramuscular, and intraperitoneal. Therapeutic administration of a polypeptide intracellularly can also be accomplished using gene therapy. The route of administration eventually chosen will depend upon a number of factors and can be ascertained by one skilled in the art.

In certain embodiments, the pharmaceutical compositions of the presently disclosed subject matter can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated. Pharmaceutically compatible binding agents, and/or adjuvant materials can be included as part of the composition. The tablets, pills, capsules, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In certain embodiments, the PTEN antagonist peptides are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In certain embodiments of the presently disclosed subject matter, a PTEN antagonist peptide, can be administered to a patient alone, or in combination with other drugs or hormones, or other agents used in the treatment of nervous system disorders as described herein or known in the art. For example, but not by way of limitation, PTEN antagonist peptides can be administered in combination with small peptides to block scar-mediated suppression, such as the peptides that block receptors of scar-generated axon growth inhibitors (29).

In certain embodiments, pharmaceutical compositions of the presently disclosed subject matter can also be prepared wherein the PTEN antagonist peptides of the disclosure are covalently or non-covalently attached to a nanoparticle. By way of example, but not limitation, a nanoparticle can be a dendrimer, such as the polyamidoamine employed in Kukowska-Latallo et al., (2005) Cancer Res., vol. 65, pp. 5317-24, which is incorporated herein by reference in its entirety. Other dendrimers that can be used in conjunction with the PTEN antagonist peptides of the instant disclosure include, but are not limited to, polypropylenimine dendrimers as described in U.S. Pat. No. 7,078,461, which is hereby incorporated by reference in its entirety.

In certain embodiments, the pharmaceutical formulations of the presently disclosed subject matter can be administered for therapeutic treatments. For example, in certain embodiments, pharmaceutical compositions of the presently disclosed subject matter are administered in a therapeutically effective amount to treat a central nervous system disorder and/or promote nerve regeneration or growth. A "therapeutically effective amount" of a substance as that term is used herein is that amount sufficient to effect beneficial or desired results, including clinical results, and, as such, a "therapeutically effective amount" depends upon the context in which it is being applied. In the context of administering a composition that promotes nerve fiber regeneration and nerve fiber growth, an effective amount of a peptide which is an antagonist to PTEN, is an amount sufficient to achieve such a modulation as compared to the nerve regeneration and/or growth obtained when there is no antagonist administered. An effective amount can be administered in one or more administrations. In certain embodiments, one or more PTEN antagonists can be administered at the same time (e.g., concurrently) or at separate times.

In certain embodiments, the dosage amount will vary from one patient to another and will depend upon a number of factors, including the overall physical condition of the patient, severity and the underlying cause of the nervous system injury. Additional factors that can be accounted for include, but are not limited to, the patient's size, body surface area, age, the particular compound to be administered, sex, time and route of administration, general health, and interaction with other drugs being concurrently administered. In certain embodiments, the dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels.

Toxicity and therapeutic efficacy of such compounds can be determined by standard pharmaceutical procedures in cell cultures or experimental animals ($LD_{50}$, the dose lethal to 50% of the population; and $ED_{50}$, the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. See, e.g., Reagan-Shaw et al. The FASEB J., 22(3):659-61 (2008). In certain embodiments, the dosage of such compounds lies within a range of circulating concentrations that include the $ED_{50}$ with little or no toxicity. The dosage varies within this range depending upon the dosage form employed, sensitivity of the patient, and the route of administration.

Methods of Using PTEN Antagonist Peptides

In certain embodiments, the presently disclosed subject matter further provides for methods of using the disclosed PTEN antagonist peptides and pharmaceutical compositions. For example, but not by way of limitation, the methods include using the disclosed PTEN antagonist peptides to treat central nervous system disorders. Non-limiting examples of central nervous system injuries include acute or chronic spinal cord injury, traumatic brain injury, stroke, multiple sclerosis, optic nerve injuries and disorders and other central nervous system disorders that damaged axons and disrupted axonal tracts. In certain embodiments, the antagonist peptides of the presently disclosed subject matter can be administered to a subject in need of nerve fiber regeneration and/or growth for any reason (e.g., as a consequence of a spinal cord injury).

In certain embodiments, the method for treating a nervous system injury includes administering a pharmaceutical composition of a therapeutically effective amount of a PTEN antagonist peptide to a subject. The disclosed subject matter also provides for methods for promoting nerve fiber growth and/or regeneration in a subject by administering a pharmaceutical composition including a therapeutically effective amount of a PTEN antagonist peptide. In certain embodiments, the methods of the present disclosure can include administering to the subject a therapeutically effective amount of two or more PTEN antagonist peptides. In certain embodiments, the methods of the present disclosure can include administering to the subject a therapeutically effective amount of one or more PTEN antagonist peptides in combination with another agent as disclosed above.

In certain embodiments, the above-described methods are practiced by administering to an individual a composition including one or more PTEN antagonist peptides to inhibit or reduce PTEN activity. Such administration can be performed singly or repeatedly over a period of time depending on the dosage and frequency as required and tolerated by the patient. In certain embodiments, the PTEN antagonist peptides of the presently disclosed subject matter are administered after diagnosis of a nervous system disorder. In certain embodiments, the PTEN antagonist peptides of the presently disclosed subject matter are administered immediately after diagnosis of a nervous system disorder. In certain embodiments, PTEN antagonist peptides can be administered within about 1 to about 48 hours following diagnosis of a nervous system disorder. For example, but not by way of limitation, PTEN antagonist peptides can be administered within about 1 to about 3 hours, about 1 to about 4 hours, about 1 to about 5 hours, about 1 to about 6 hours, about 1 to about 12 hours, about 1 to about 18 hours, about 1 to about 24 hours, about 1 to about 48 hours, about 2 to about 48 hours, about 3 to about 48 hours, about 4 to about 48 hours, about 5 to about 48 hours, about 6 to about 48 hours, about 12 to about 48 hours, about 18 to about 48 hours or about 24 to about 48 hours following diagnosis of a nervous system disorder.

In certain embodiments, the PTEN antagonist peptides of the presently disclosed subject matter are administered once, twice, or three, four, five, or six times per week, or daily. In certain embodiments, PTEN antagonist peptides of the presently disclosed subject matter are administered daily for a time period of about 2 weeks. In certain embodiments, the PTEN antagonist peptides of the presently disclosed subject matter can be administered one or more times per day. For example, but not by way of limitation, an exemplary pharmaceutical formulation for oral administration, intravenous injection or subcutaneous injection can be in a daily amount of between about 0.1 to 0.5 to about 20, 50, 100, 500, 1,000, 3,000 or 4,000 or 10,000 or 20,000 or more g per kilogram of body weight per day of peptide. In certain embodiments, a pharmaceutical formulation for oral administration, intravenous injection or subcutaneous injection can be in a daily amount of between about 0.5 to about 20 mg of PTEN antagonist peptide per kilogram of body weight per day.

Kits

In certain embodiments, the present subject matter also contemplates kits including a composition including a PTEN antagonist peptide. In certain embodiments, the composition can include more than one PTEN antagonist peptide. The antagonist(s) can be in any state suitable for packing in a kit, such as lyophilized or resuspended in a pharmaceutically acceptable excipient. The kit can further include instructions for use, such as dosing regimen and/or adjuvants that can be used with the composition(s).

The following Example is offered for the purpose of illustrating the disclosed subject matter and is not to be construed as a limitation.

Example: Systemic Peptide Antagonist Peptides Promote Axon Growth and Recovery after Spinal Cord Injury Materials and Methods Sources of Compounds.

Antibodies against the following proteins were used: PTEN (13806) rabbit mAb, phospho-Akt (Ser473, 587Fl1) mouse mAb, Akt (pan, 11E7) rabbit mAb, phospho-GSK 3β (Ser9), GSK-3β (27C10) rabbit mAb (1:1000), phospho-S6 ribosomal protein (Ser235/236) rabbit mAb, phospho-Erk1/2 (p44/42, Cell Signaling Technology), 5-HT serotonin rabbit (1:4000, ImmunoStar), monoclonal anti-GFAP (1:400, Sigma), neuron-specific class III β-tubulin (Tuj1, 1:500, Covance), mouse myelin basic protein (MBP, SMI 99, Convence) and goat anti-biotin agarose (Vector Lab). The major proteins employed include the purified myelin from bovine brain white matter (Pel-Freez Biologicals), laminin (Sigma) and ABC kit (PK-6100, Vector Lab). The PTEN plasmid was purchased from Addgene and amplified in the lab. The RP and PTEN antagonist peptides were designed in a lab and synthesized by CHI Scientific and their purity was analyzed via HPLC. The biotinylated peptides were made with E:Z-Link Sulfo-NHS-LC-LC-Biotin and dialyzed with Tube-O-Dialyzer™, Micro (1K MWCO, G-Bioscience) following protocols from the manufacturer.

Neurite Outgrowth Assay in Primary Neuronal Cultures.

Neurite outgrowth from neurons was performed in DRG and CGN cultures 1-5 days after growth. For DRG assay on myelin spots, the center of each culture coverslip was spotted with 2 μl of purified CNS myelin (200 μg/ml), which contains a number of axon growth inhibitors (11). DRGs were dissected out from C57BL/6 mice aged 8-10 weeks. After incubation with collagenase and 0.25% trypsin, dissociated DRG neurons were plated onto plastic coverslips in 24-well plates and grown in culture medium as previously reported (25, 48). Primary CGN cultures were prepared from cerebelli of postnatal 7-9 day C57BL/6 mice as reported previously (25, 29).

After plating, dissociated neurons were treated with vehicle, RP (10 μg/ml), PAP1 (2.5 μg/ml), PAP2 (10 μg/ml), PAP3 (6.7 μp/ml), PAP4 (6.7 μg/ml) and PAP5 (5 μg/ml). The doses of PAPs were chosen based on the dose-response curve obtained from neurite outgrowth assays of DRGs on CNS myelin. Neurons were fixed 5 days (DRGs) or 24 hrs (CGNs) after plating and stained for Tuj1. Images of each culture were captured with a Nikon image collecting system and neurite outgrowth was quantified with Photoshop and NIH image software (25). The total neurite length of DRGs per myelin spot was determined from 5-8 representative experiments. The neurite length of CGNs was measured as previously reported (25, 29). To determine the cellular distribution of PTEN, DRGs were stained with anti-PTEN and anti-Tuj11 antibodies in selected coverslips.

PTEN Peptide Binding Assay in COS-7 Cells.

COS-7 cells were cultured as previously reported (29). Forty-eight hrs after transfection, cells were incubated with purified biotinylated RP or PAPs 1-4 (15 μM) for 1 hour. Following 3 washes with PBS and fixation with 4% formaldehyde, COS-7 cells were incubated in ABC and the PAP binding signals were visualized with ABC-DAB based color reactions. The intensity of reaction color in multiple wells was read with a 96-well plate reader at 405 nm. The binding experiments were carried out in 6-12 replicates.

PTEN, Akt, GSK-3β, S6 Kinase and Erk Assays in the Lesioned Spinal Cord.

To detect the potential changes of PTEN signaling pathway in vivo, a dorsal transection injury at T7 (see below) was performed in 5 groups of adult mice (3 mice/group) and collected fresh spinal cord 1, 3, 7, 14 and 21 days after SCI for biochemistry. At different time points after injury, mice were perfused through heart with cold PBS and the fresh spinal cord blocks containing the injury site (2 mm rostral to and 2 mm caudal to the injury) 2-6 mm rostral to lesion and 2-6 mm caudal to lesion were harvested immediately after perfusion. In addition, 3 age-matched adult female mice received sham surgery and were used as no-injury controls. Tissues were prepared in lysis-buffer supplemented with protease inhibitors (1 mM phenylmethylsulfonyl fluoride, 2 mM orthovanadate, 10 μg/ml leupeptin and 10 μg/ml aprotinin). Following total protein quantification in supernatants, samples containing the same amount of proteins were prepared for Western blots using antibodies against PTEN, p-S6, p-Erk, p-Akt, p-GSK, total Akt (t-Akt), GSK 3β (t-GSK) and actin. The levels of phosphorylated Akt, S6 and Erk1/2 represent active form of these proteins, but p-GSK indicates the inactive form of this kinase. For band densitometry, the images of protein bands were captured with a BioRad Gel Doc XR documentation system and band density was determined using Quantity One software (25). The values of band density measured from different time points after SCI were compared to those in no injury controls.

To evaluate potential role of PAPs in blocking PTEN signaling pathway in vivo, a dorsal transection injury at T7 was also performed in the other 5 groups of adult mice (4 mice/group, FIG. 4). Two hours after injury, mice received treatment with RP, PAP1, PAP2, PAP3 or PAP4 (71 μg/mouse/day) for two days. Forty-eight hours after SCI, mice were perfused through heart with cold PBS and the fresh spinal cord blocks containing the injury site (2 mm rostral to and 2 mm caudal to the Injury) were harvested immediately after perfusion. In addition, 4 age-matched adult female mice received sham surgery and were used as no-injury controls. Tissues were prepared in lysis buffer supplemented with protease inhibitors. Samples containing the same amount of proteins in tissue supernatants were employed for p-Akt, p-GSK, p-S6, t-Akt, t-GSK and actin (FIG. 4) via Western blots as described above. The values of band density measured from different peptide treatments were compared to those treated with RP.

Dorsal Over-Hemisection of the Spinal Cord, Peptide Treatments, Peptide Penetration, Histology and Behavioral Tests in Mice.

Adult female C57BL/6 mice (9-10 weeks old) were deeply anesthetized with intramuscular ketamine (100 mg/kg) and intraperitoneal xylazine (15 mg/kg). A complete laminectomy was performed and the dorsal part of the spinal cord was fully exposed at T6 and T7 levels (31). A dorsal over-hemisection (1.0 mm) was performed at T7 with a 30 gauge needle and a pair of microscissors to completely sever dorsal part of the spinal cord as previously reported (29, 31). To study axon growth (FIG. 5-7), mice received daily subcutaneous injections of RP, PAP2 or PAP4 at 71 μg/mouse/day beginning two days after SCI for 14 successive days (29). Mice received BDA tracer injections into the motor cortex 3 weeks after SCI (31).

Mice were perfused 5 weeks after SCI and the spinal cord blocks around the lesion were processed for 5-HT and CST labeling. In brief, transverse sections (30 μm) 5-7 mm rostral to and caudal to the injury and parasagittal sections 4 mm rostral to and 4 mm caudal to lesion were processed for 5-HT-stained serotonergic fibers and BDA-labeled CST axons. To compare axon number among different groups, 5-HT axons were counted in the spinal cord 0-3.2 mm caudal to the lesion from all parasagittal sections in each animal. To determine functional recovery, locomotion recovery was evaluated during 5 weeks of survival by measuring the BMS two days and per week after SCI, and the grid walk performance and footprint 5 weeks after SCI. For axon quantification and behavioral analysis, 8, 9, and 9 mice were used in the RP, PAP2 and PAP4 groups, respectively.

Figures 8A, 8B:
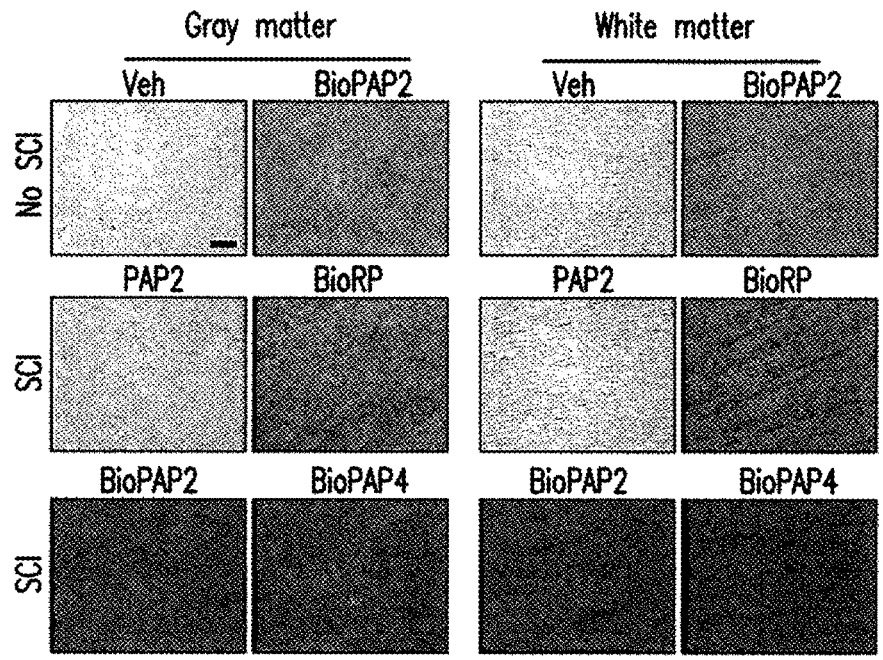
FIG. 8A-C. Biotinylated PAP2 and PAP4 penetrate into the spinal cord in mice with T7 dorsal transection. One day after treatments, SCI mice were perfused and biotin labeling signals were examined from parasagittal sections of fixed spinal cord around the lesion (2 mm rostral and 2 mm caudal to injury, 4 mm long). Treatments with biotinylated PAP2 and PAP4 induced stronger staining signals for biotin in the gray matter (A) and white matter (B) of the spinal cord than control groups. Scale: 25 µm. C, Biotin-conjugated peptides were pulled down from tissue lysates of fresh spinal cord blocks with anti-biotin beads and biotin signals were measured with ABC-DAB color reactions. Higher biotin signals were detected in mice treated with BioRP, BioPAP2 (BioP2) or BioPAP4 (BioP4), but not with non-biotin-labeled PAP2 (P2), suggesting efficient penetration of peptides into the lesioned spinal cord. Means±SEM were shown and the differences indicated were compared to PAP2-treated SCl controls. *<0.05, n=3 mice per group.

For peptide penetration experiments mice received vehicle DMSO, PAP2, or biotinylated RP (BioRP), BioPAP2 or BioPAP4 (subcutaneous injection, 71 μg/mouse) two hours after the lesion. They received the 2nd treatment 12 hours after SCI and were perfused for histology 24 hrs after SCI. To detect biotin signal along the spinal cord, parasagittal sections of the fixed spinal cord 2 mm rostral to and caudal to the lesion (4 mm long in total) were cut and processed for biotin labeled signaling with ABC-DABbased color reaction (FIG. 8A, B, 3 mice/group). In separate animals (FIG. 8C, 3 mice/group), the fresh spinal cord blocks 2 mm rostral to and caudal to the lesion were harvested immediately after perfusion with cold PBS. BioRP and BioPAPs in the supernatants of spinal cord lysates were precipitated with anti-biotin beads and measured with ABC-DAB-based reactions.

Statistical Analysis.

SigmaPlot software was used for statistical analysis. Data in graph are shown as means±SEM. Student's t-test was used for experiments involving a single determination of means between two independent groups. A repeated measures ANOVA was used for the BMS data analysis. Statistical significance for other analyses was tested with the unpaired Student's t-test with Welch's correction or Mann-Whitney modification. Differences between groups with $p<0.05$ were considered significant.

Results

Design of PTEN Antagonist Peptides.

Peptides derived from the active regions of a protein often selectively interact with the same molecule and potently alter its activity. To selectively block PTEN function with a pharmacological approach, five PTEN antagonist peptides (PAP) were designed by targeting the phosphatidylinositol-4,5-bisphosphate (PIP2), ATP-type A or B, PDZ and PDZ recognizing regions of PTEN (FIG. 1A, Table 1) (22, 23). To facilitate their access into cells, the transactivator of transcription (TAT) sequence (GRKKRRQRRRC (SEQ ID NO:6)) was included at the C-terminus of all the PAPs. Given that TAT-fusion proteins retain their biological activity and are able to rapidly and efficiently access the intracellular space of cultured cells and intact tissues following extracellular applications in vitro and in vivo (24), the TAT-containing PAPs should efficiently penetrate into cells after extracellular administration.

PTEN Antagonist Peptides 1-4 Overcome Growth Restriction of Neurites on Inhibitory Substrates.

Figure 1B:
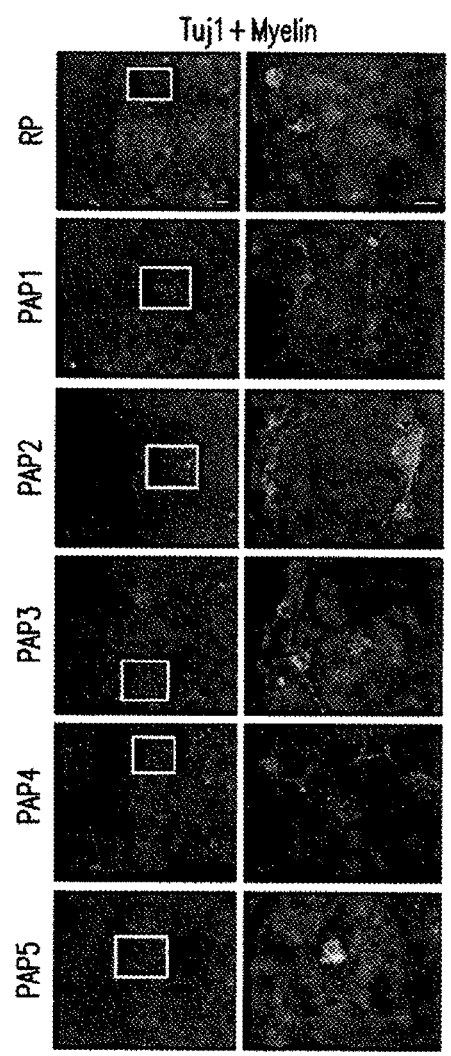
Figure 1C:
Figure 1D:
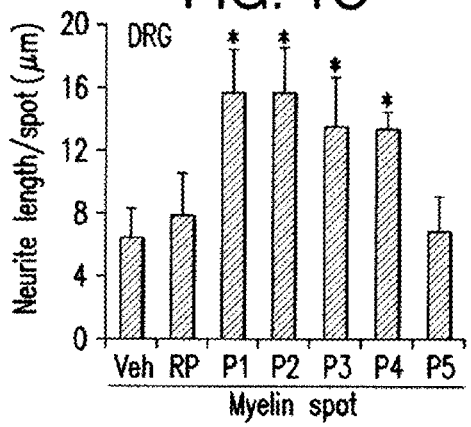
Figure 1E:
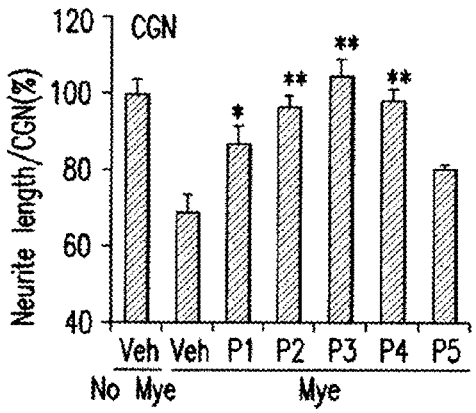

To test whether PTEN blockade with PAPs promotes neurite outgrowth in vitro, axon growth of adult DRG neurons cultured in the presence of axon growth inhibitors was evaluated. Use of mature neurons should be relevant to repair of CNS axonal injuries in humans. Neurite elongation of dissociated DRGs was assessed using a spot assay of purified CNS myelin, which contains a number of axon growth inhibitors (11). Following 5 days of neuronal growth, the length of neurites present on the myelin spots was measured. These neurites originated from neuronal perikarya either outside or inside of myelin spots. Although a very high density of neurites was detected on all the coverslips, a limited number of neurites were present on myelin spots under control conditions (FIG. 1B). In contrast, treatments with PAPs 1-4 (2.5-10 µg/ml), but not with PAP5 (5 µg/ml), significantly enhanced the number of neurites on myelin spots (FIG. 1B, D). PAPs 1-4 showed a similar growth-promoting effect on neurite extension on highly concentrated CNS myelin (200 µg/ml). Double immunostaining confirmed the expression of PTEN in the cell bodies and neurites of DRGs (FIG. 1C). To confirm the PTEN blocking activity of PAPs, neurite growth of cultured cerebellar granular neurons (CGNs), a type of central neuron, derived from postnatal 7-9 day mice was assessed (25). Like DRG neurons, CGNs are sensitive to myelin inhibitors (25). While PAPs 1-4 target different domains of PTEN, they induced a similar degree of neurite extension of CGNs on coverslips evenly coated with purified CNS myelin (50 µg/ml, FIG. 1E). Thus, out of the 5 PTEN-targeting peptides, PAPs 1-4 at low M doses significantly promoted axon elongation on inhibitory substrates in vitro.

PAPs 1-4 Significantly Bind to PTEN Protein Expressed in COS-7 Cells.

Figure 2B:
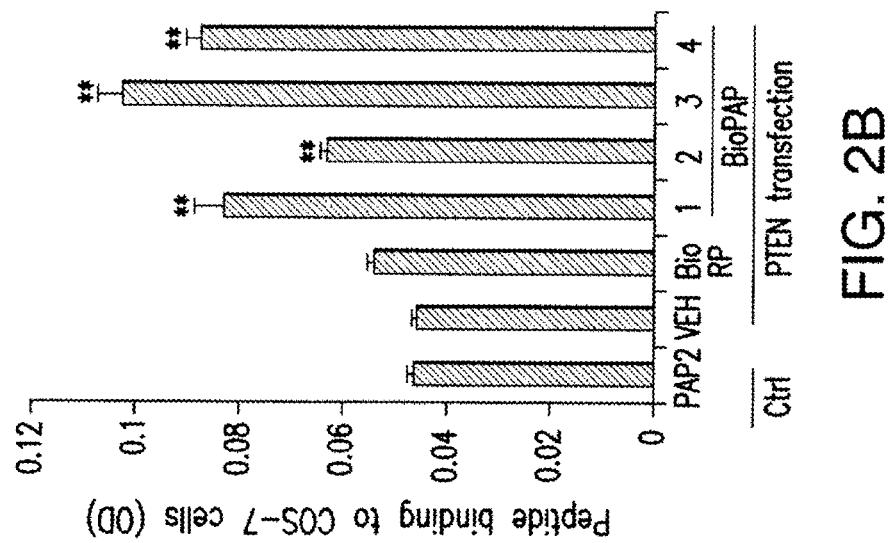
FIG. 2A-D. PAPs 1-4 significantly bind PTEN protein in transfected COS-7 cells. A, COS-7 cells were transfected with control or PTEN plasmid. Forty-eight hours after transfection, cells were incubated with purified PAP2, BioRP or BioPAPs 1-4. Peptide-binding signals were detected by staining biotin with ABC-DAB based color reactions. Scale: 50 µm. B, Bar graph indicates the quantified peptide binding signals in each group with a 96-well plate reader at 405 nm. The differences indicated are compared to BioRP-treated control (**<0.01, Student's t test. n=6 wells in each group). C, Western blot confirmed expression of PTEN in transfected COS-7 cells. D, The representative images indicated expression of PTEN in COST-cells. Scale: 25 µm.
Figure 2A:
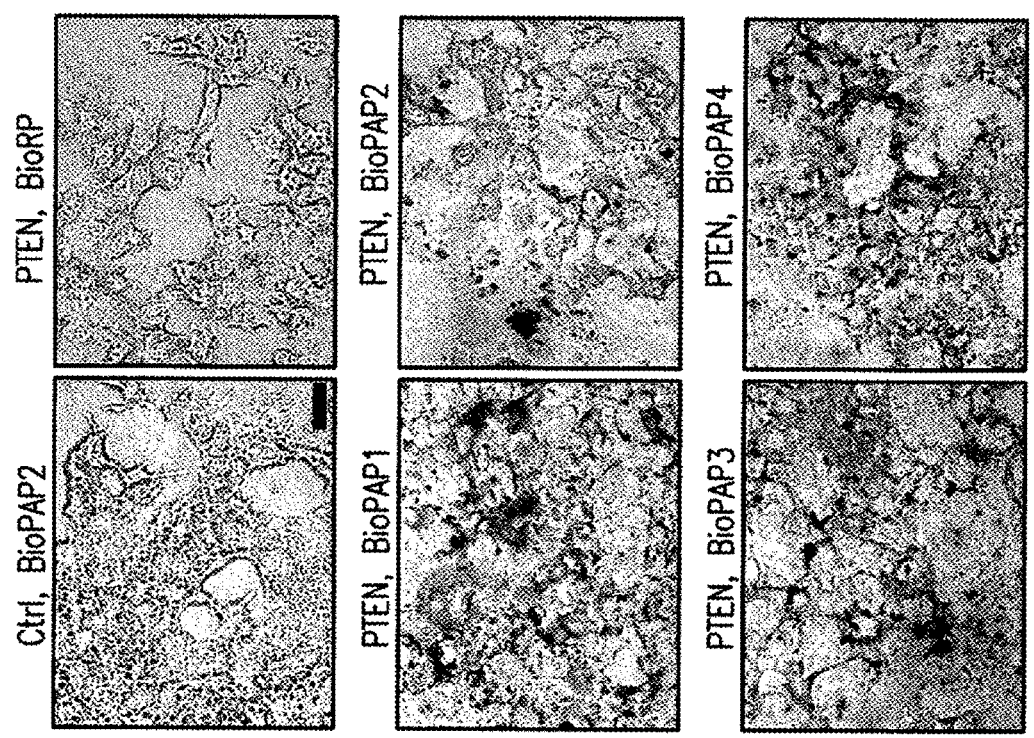
Figure 2C:
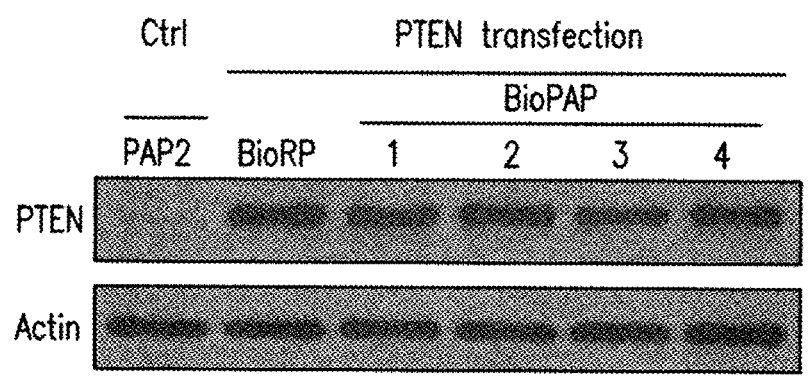
Figure 2D:
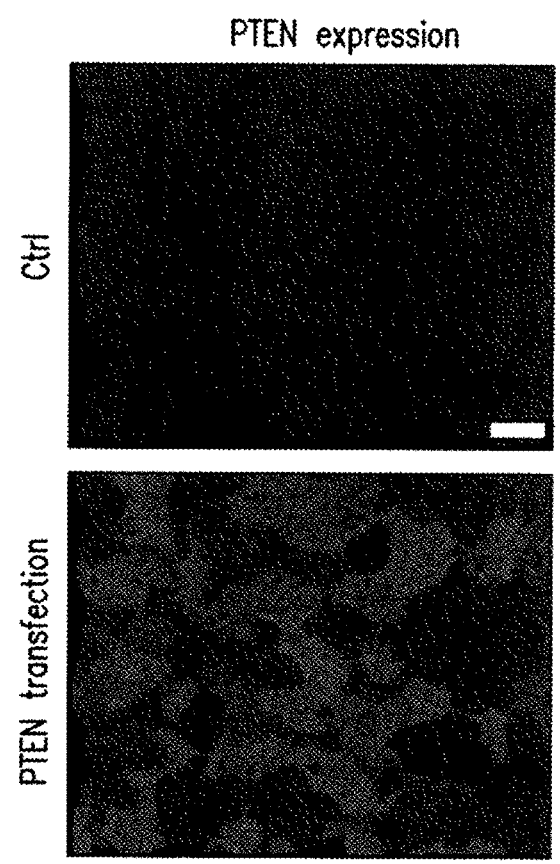

To confirm the interactions between PAPs and PTEN protein, a peptide binding assay for PTEN expressed in non-neuronal COS-7 cells two days after transfection was performed. After incubation with purified biotinylated random sequence peptide (BioRP) or PAPs (BioPAP, 15 µM), peptide binding was evaluated by measuring biotin signals with avidin/biotin complex (ABC)-diaminobenzidine (DAB)-based color reactions. A weak baseline staining was detected in control DNA-transfected cells probably due to low level of endogenous PTEN expression in COS-7 cells. However, PAPs 1-4 cells exhibited the dramatically enhanced binding to cells transfected with PTEN (FIG. 2A, B). PAPs 1, 3 and 4 revealed higher binding affinity than PAP2 at 15 µM. The increased binding of peptides was due to PTEN expression (FIG. 2C, D) because COS-7 cells transfected with control DNA did not display enhanced binding to BioPAP2.

Traumatic Injury Altered PTEN Expression and Increased S6 and Erk Activity in the Spinal Cord.

Figures 3A, 3B, 3C:
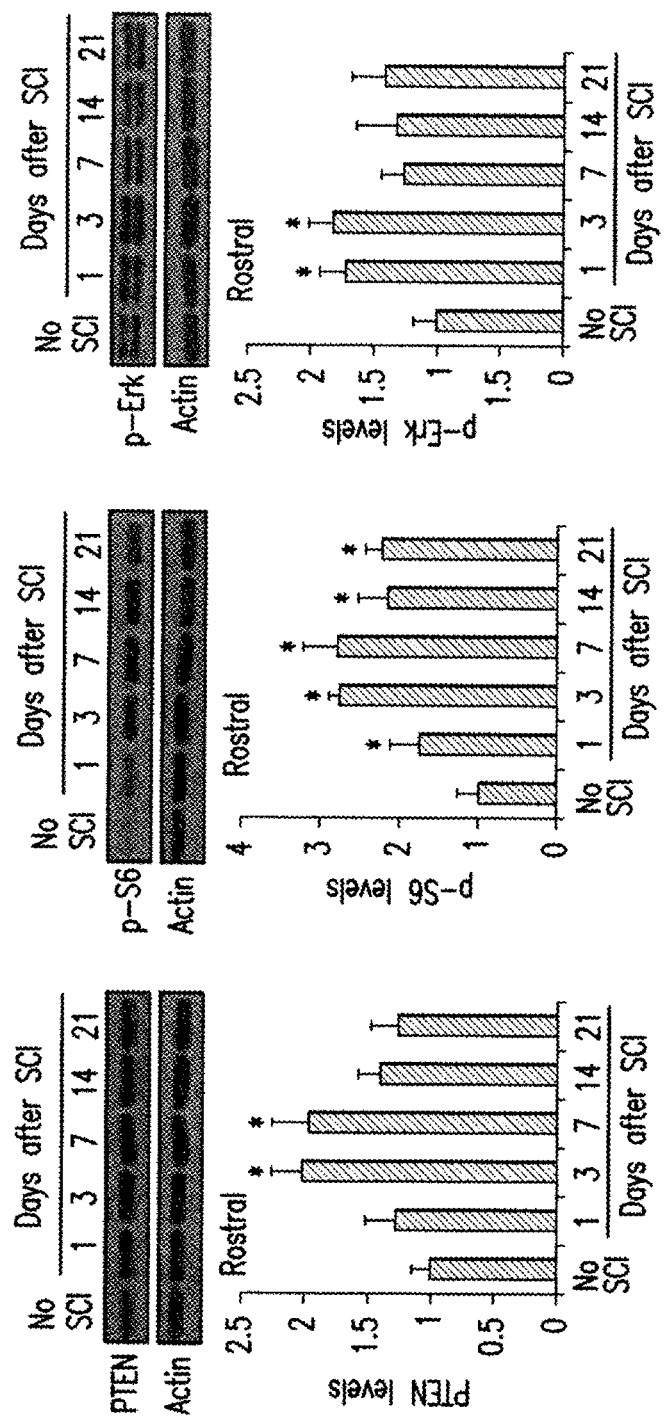
Figures 3D, 3E, 3F:
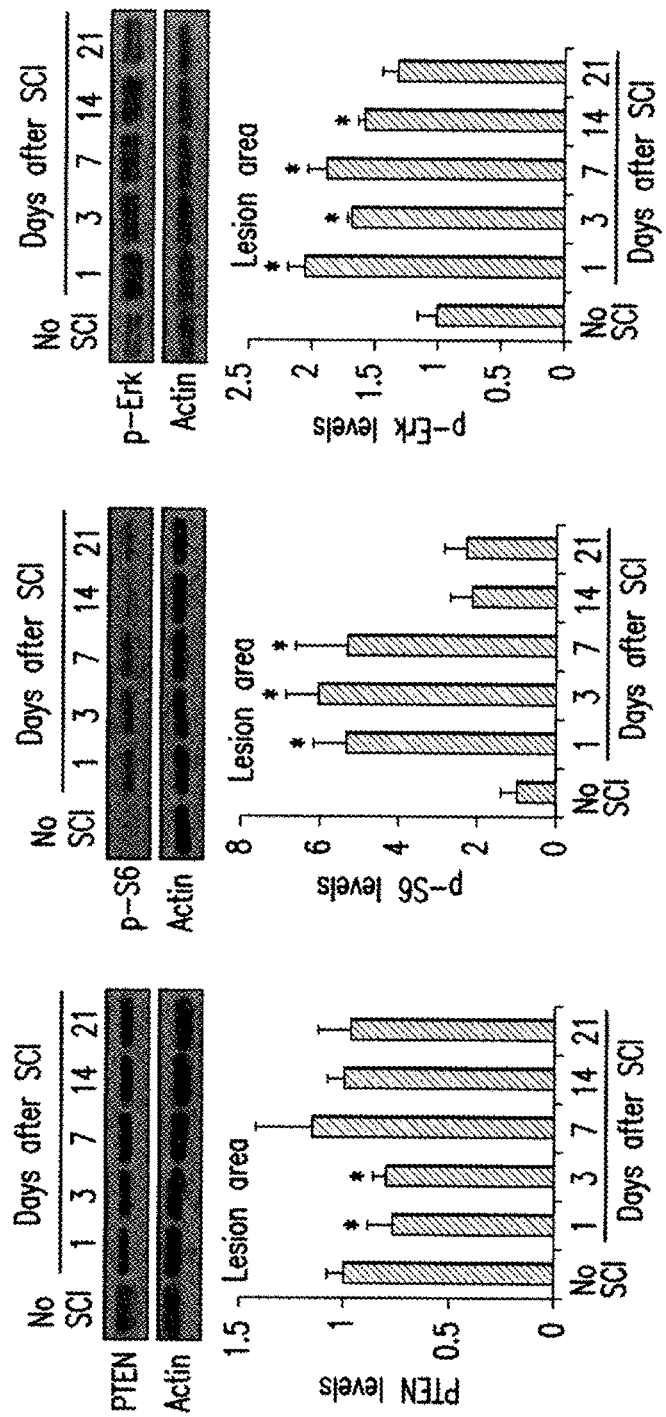

To determine whether spinal cord trauma resulted in expression change of PTEN protein and its downstream signaling pathway), the levels of PTEN phosphorylated S6 (p-S6) and Erk (p-Erk) in the lesioned spinal cord were examined 1-21 days after injury. Enhanced PTEN expression was detected in the rostral spinal cord 3-7 days after SCI although lesion moderately reduced PTEN in the lesion center area (FIG. 3A, D, G). As the downstream pathway of Akt/PTEN, mTOR kinase is critical for regulating neuronal growth (14). One of the well-studied mTOR targets is ribosomal S6 kinase 1, which phosphorylates ribosomal protein S6. The cellular levels of p-S6 properly represent mTOR activity (14). Also, PTEN could prevent Erk activation via acting FAK, a direct protein substrate (26). Thus, the alterations of p-S6 and p-Erk in the lesioned spinal cord were monitored, in addition to PTEN. Although a degree of p-Erk in the un-injured spinal cord was detected (FIG. 3C F, I), the basic level of p-S6 in the un-injured spinal cord is very low (FIG. 3B, E, H). Lesion significantly increased the levels of both p-S6 and p-Erk, especially 1-7 days after trauma. These findings are evidence that PTEN inactivation and mTOR activation several days after SCI. The enhanced p-S6 and p-Erk signals may occur in neuronal and/or glial cells.

PAPs 1-4 Activate Akt and S6, but Inactivate Glycogen Synthase Kinase 3β (GSK-3β) in the Injured Spinal Cord.

To validate biological activity of PAPs 1-4 in vivo, the downstream signaling changes of PTEN in injured spinal cord following systemic PAP treatments were examined. Akt, GSK-3β and S6 are the best-characterized downstream signals of PTBN and measurement of phosphorylated Akt, GSK-3 and S6 is widely used to determine PTEN and mTOR activities (14, 27, 28). Akt phosphorylation at residue Ser473 (p-Akt) in the C-terminal hydrophobic motif is necessary for full activation of this signaling and the cellular levels of p-Akt at Ser473 represent its activity. GSK-3β is constitutively active in neurons under resting conditions and is inactivated by extracellular signals through phosphorylation of an N-terminal serine residue at Ser-9. The levels of phosphorylated GSK-3β at Ser9 (p-GSK) are inversely correlated with GSK-3β activity in neurons (28). Phosphorylation of S6 ribosomal protein highly correlates with increased translation of mRNA transcripts and cell growth.

Thus, the levels of p-Akt, p-GSK and p-S6 were examined in lysates of the spinal cord 48 hrs after a T7 dorsal over-hemisection in adult mice. The p-Akt and p-GSK levels in the injured spinal cord of RP-treated animals were not significantly altered 48 hrs after lesioning compared to the un-injured controls (FIG. 4). In contrast, the spinal cord in SCI mice systemically treated with PAPs 1-4 (71 μg/mouse/day) exhibited higher levels of p-Akt, p-GSK and p-S6 than the RP-treated SCI controls. Therefore, treatments with PAPs 1-4 efficiently activate Akt and mTOR, and inactivate GSK-3β in the lesioned spinal cord, supporting the efficient biological activity of PAPs.

Systemic PAP2 and PAP4 Treatments Stimulate Growth of Descending Raphespinal and CST Fiber Tracts in Mice with T7 Dorsal Over-Hemisection.

Figure 5B:
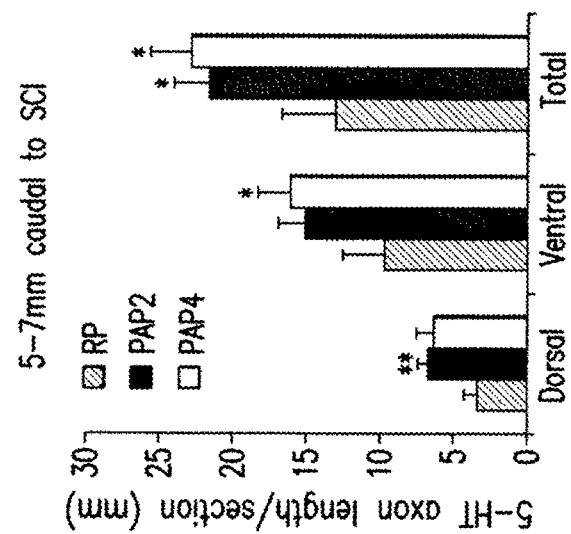
FIG. 5A-D. Systemic treatments with PAP2 and PAP4 enhance serotonergic fibers in the caudal spinal cord in SCI mice. A, Transverse sections of the spinal cord S-7 mm caudal to the lesion at upper lumbar levels displayed reduced 5-HT fibers 5 weeks after dorsal transection at T7, but treatments with PAP2 or PAP4 increased the density of serotonergic fibers in central and ventral part of the spinal cord compared to RP-treated mice. Scale bar: 50 m. B, Serotonergic fiber length was measured from the gray and white matter in dorso-central areas and from the gray matter in ventral horn of the spinal cord 5-7 mm caudal to the lesion. The animals from RP group show a number of 5-HT axons in the distal spinal cord, indicating the spared serotonin axons following dorsal over transection. In contrast, subcutaneous injections of PAP2 or PAP4 started 2 days after SCI resulted in a greater number of 5-HT axons in the distal spinal cord, particularly in the ventral areas. The dorsal is up in all these sections. C, Camera lucida drawings of 5-HT fibers from all parasagittal sections of the representative mouse in each group are shown from the RP, PAP2 and PAP4-treated animals. Scale: 200 m. D, Serotonergic fiber number was counted from all parasagittal sections of the spinal cord 0-3.2 mm caudal to the lesion epicenter in each group. In B and D, means±SEM were shown and the differences were compared to RP-treated SCI controls. *p<0.05, **p<0.01.
Figure 5A:
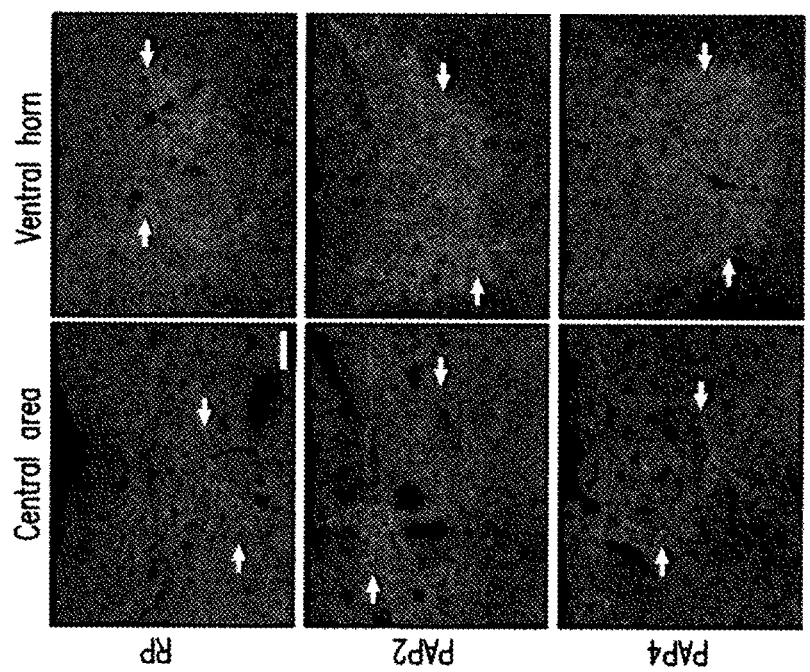
Figure 5D:
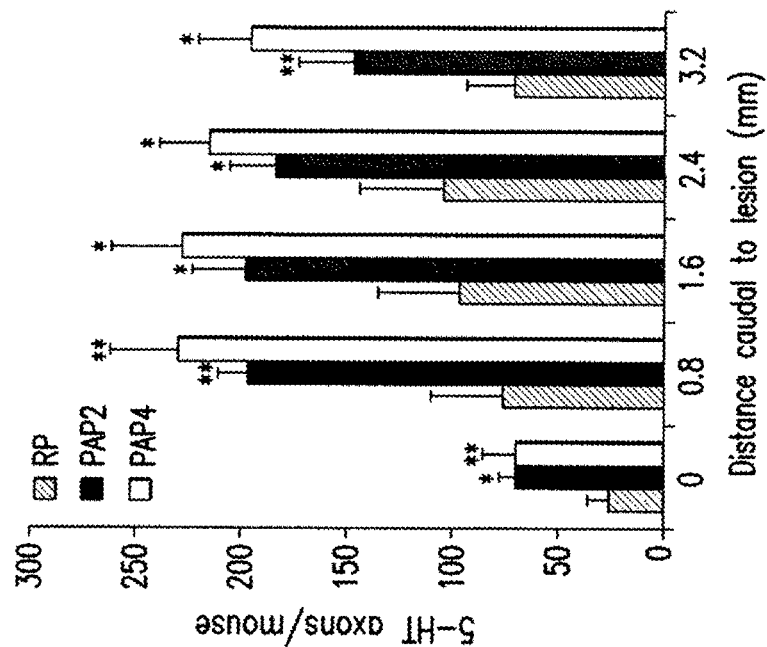
Figure 5C:
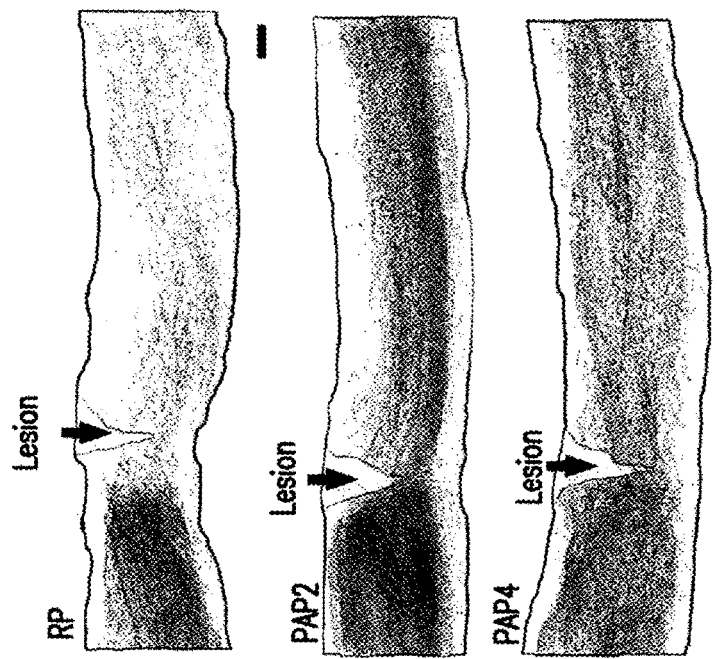

PTEN suppression with PAPs was analyzed to determine if such suppression would stimulate axon growth and functional recovery dorsal over-hemisection SCI at T7, a model that disconnects a group of defined pathways (29). Because PAPs 1-4 exhibited similar growth-promoting actions in vitro (FIG. 1), two peptides were randomly chosen, PAPs 2 and 4, and evaluated for their axon growth-promoting potential following daily subcutaneous injections for 14 consecutive days initiated 2 days after SCI. We characterized descending serotonergic fibers from transverse sections of the spinal cord by immunostaining 5-HT. The 5-HT tracts contribute to behavioral recovery after SCI (30). Five weeks after dorsal over-hemisection, the density of 5-HT fibers was dramatically reduced in the caudal spinal cord compared to sections rostral to the lesion (31). However, SCI mice treated with PAPs 2 and 4, the density of 5-HT fibers in the spinal cord 5-7 mm caudal to the lesion was significantly increased compared to RP-treated SCI controls (FIG. 5A, B) although the density of 5-HT fiber 5-7 mm rostral to the lesion was similar among different groups. Parasagittal sections containing the lesion site also displayed projection of a greater number of 5-HT axons into the lesion areas and the caudal spinal cord in the PAP-treated mice (FIG. 5C, D).

Figure 6A:
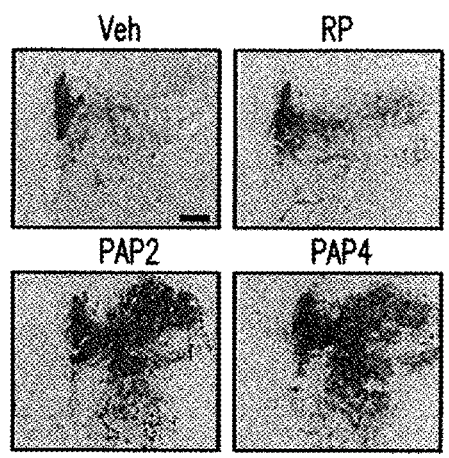
FIG. 6A-E. PAP2 and PAP4 treatments induce CST sprouting rostral to the lesion and limited growth caudal to the lesion in SCI mice. A, Transverse sections 5-7 mm rostral to the lesion display a similar degree of dorsal CST labeling in SCI mice. The midline is to the left and dorsal is up in all the sections. Increased density of ectopic sprouts lateral to the dorsal CST was detected in the PAP2 and PAP4 treated animals. Scale: 50 µm. B, Ectopic CST sprouts outside of the dorsal CST were quantified from transverse sections 5-7 mm rostral to injury (means±SEM). C, Parasagittal sections around the lesion in SCI controls indicated termination of dorsal CST axons and a number of CST sprouts immediately rostral to the lesion. D, Similar sections around the lesion in PAP2-treated mice indicated higher density of CST sprouts immediately rostral to the lesion. A small number of CST sprouts grew into the distal spinal cord. E, Parasagittal sections from a PAP4-treated mouse near the lesion indicated a very high density of CST sprouts immediately rostral to the lesion, but they terminated rostral to the lesion epicenter. The bottom images in C, D and E indicated GFAP staining and lesion areas in these sections. Scales in C, D and E: 200 m for the top and bottom images, and m for the middle images.
Figure 6B:
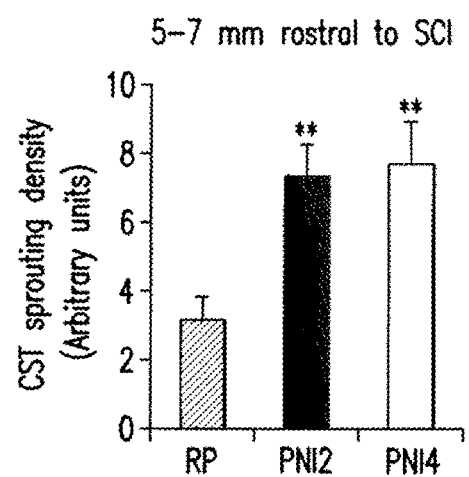

PTEN deletion has been reported to promote compensatory sprouting and impressive regeneration of CST axons in SCI mice (16). The integrity of CST tracts, which appear to contribute to fine voluntary movements of the limbs (32), was also evaluated. In RP-treated animals, the prominent dorsal CST is tightly bundled rostral to the lesion and a few dorsolateral fibers are visible at the ipsilateral site (FIG. 6A). A number of biotin dextran amine (BDA)-labeled CST collateral sprouts projected into the gray matter, particularly in the ventral portion. The sprouting was primarily confined to the side of spinal cord contralateral to tracer injection. In contrast, rostral sections from PAP-treated SCI animals exhibited a different BDA labeling pattern because a higher density of BDA-labeled fibers outside of dorsal CST was detected. Ectopic CST fibers extended throughout the gray matter area in most PAP-treated mice and some fibers reached into the lateral and dorsolateral white matter. Moreover, a greater number of CST sprouts extended into the gray matter of opposite spinal cord ipsilateral to the tracer injection site. Quantification of the collateral CST sprouts from transverse sections indicated a 2-fold increase in the PAP-treated animals (FIG. 6B).

Figures 6C, 6D, 6E:
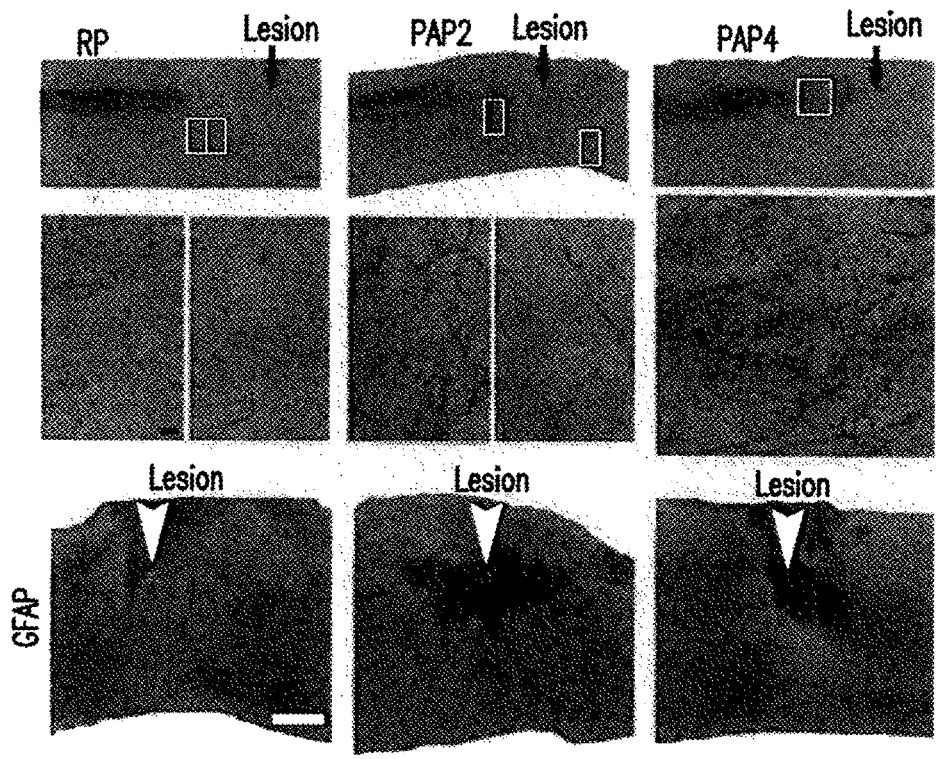

One issue to be addressed is whether pharmacological PTEN blockade stimulates growth of CST axons into and beyond the lesion area after SCI. To that end, BDA-traced CST fibers were examined in parasagittal sections around the lesions, which were visualized by glial fibrillary acidic protein (GFAP) staining. CST fibers terminated a few mm rostral to the lesions and did not regenerate into the caudal spinal cord in RP-treated mice (FIG. 6C). No ventral CST axons were observed in these mice. However, sections from PAP treated mice displayed a higher density of CST sprouts immediately rostral to the injury and some sprouts approached to lesion epicenter (FIG. 6D, E). A small number of CST axons bypassed the lesion epicenter and projected into the caudal spinal cord (FIG. 6D). GFAP staining around the lesion indicates similar transection injury in these animals (bottom images in FIGS. 6 C, D and E). These fibers appear to be regenerating axons because they exhibited highly branching patterns in gray matter areas and were only observed in PAP treated mice. Thus, only a few CST axons grew into the caudal spinal cord although PAP treatments stimulated remarkable CST sprouting rostral to the lesion.

PAP Treatments Significantly Improve Recovery of Locomotor Function in SCI Mice.

Figure 7C:
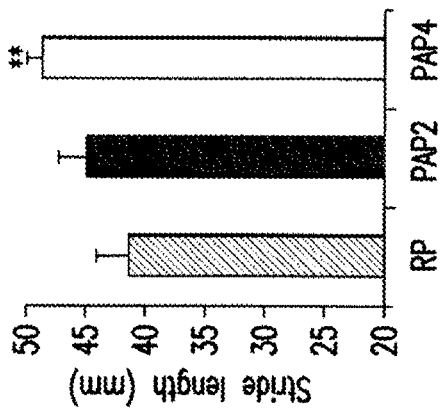
FIG. 7A-D. Systemic treatments with PAP2 and PAP4 improve locomotor recovery in SCI mice. A, Graph indicates the locomotor BMS scores in RP-(black color), PAP2-(red) or PAP4-treated (green) mice following T7 dorsal transection SCI. B, Graph indicates grid walk errors in RP (black), PAP2 (red) or PAP4-treated (green) mice 5 weeks after SCI. C, Graph indicates stride length of the hindlimbs 5 weeks after injury in 3 groups. D, The representative footprints of the hindlimbs are shown from 3 groups of mice. Means±SEM were shown and the differences indicated were compared to RP-treated SCI controls. *p<0.05; **p<0.01.
Figure 7B:
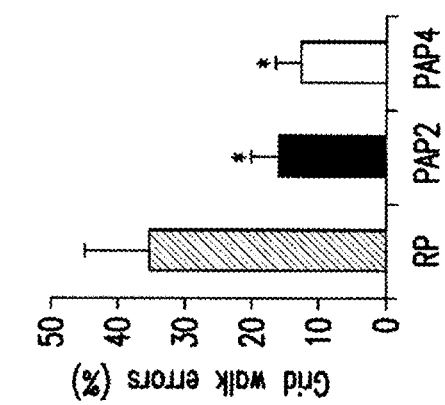
Figure 7A:
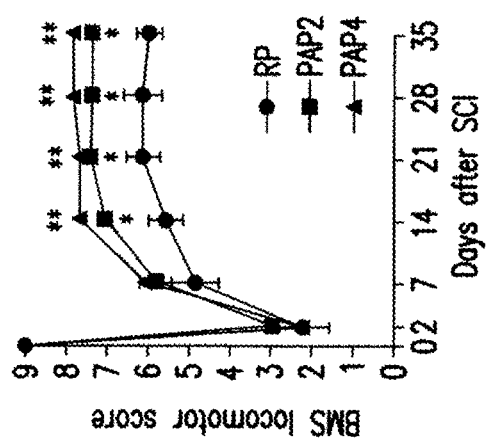
Figure 7D:
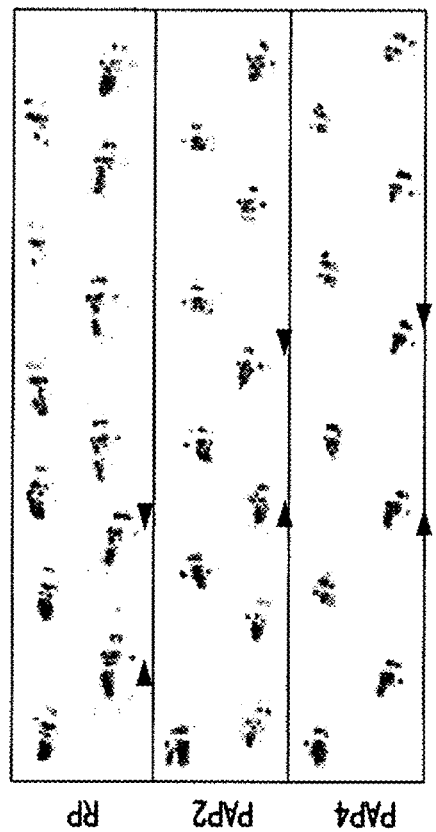

Functional recovery in these SCI mice were evaluated by measuring the standardized Basso mouse scale for locomotion (BMS) locomotor scores, grid walk and footprints of the hindpaws (29, 31, 33). Two days after dorsal over-hemisection, mice showed no observable or slight-extensive hindlimb movement (BMS: 0-3, FIG. 7A). The RP treated controls exhibited partial recovery several weeks after SCI, probably due to short-range sprouting of spared fibers and reorganization of segmental circuitry, including propriospinal re-connections (34). The recovery reached a stable level by ~3 weeks after lesioning and mice generally had some coordination and hind paw rotation when making initial contact with the testing surface and on lift off. In contrast, the PAP treated mice exhibited increased BMS scores 2-5 weeks after SCI and most had consistent coordination and parallel paw position when contacting the testing surface (FIG. 7A). A grid walking test was also performed by evaluating the incidence of the hindlimbs slipping below the grid plane from videotapes watched at a slow speed 5 weeks after SCI. The RP treated SCI mice made numerous errors by misplacing their hindpaws and falling into grid holes, but the PAP-treated mice made significantly fewer errors by correctly placing their hindpaws on the grid (FIG. 7B). Moreover, PAP4-treated mice had enhanced stride length of the hindpaws measured from footprints 5 weeks after injury (FIG. 7C, D). Together, PAP2 and 4 treatments significantly improve growth of descending fiber tracts amid recovery of locomotor function in adult rodents with SCI.

PAP2 and PAP4 Penetrated into Lesioned Spinal Cord Following Systemic Administration in Mice.

Figure 8C:
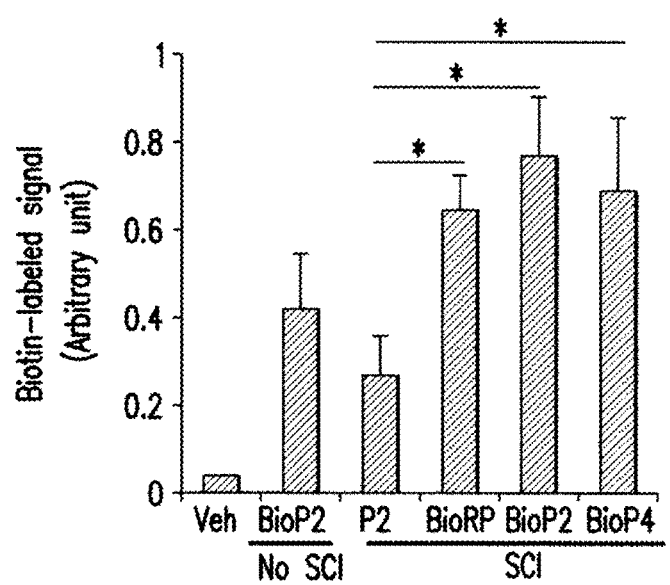

Following SCI, there is breakdown of the blood-brain barrier around the lesion for weeks to months (35), which could permit penetration of peptides into the CNS following systemic administration. Conjugation of the TAT sequence to PAPs should further facilitate their penetration into the CNS and cells (36). To confirm access of PAPs into injured spinal cord, distribution of BioPAP2 and BioPAP4 in mice with T7 dorsal transection were examined one day after subcutaneous peptide delivery by measured biotin-labeled signals with color-based reactions. Stronger biotin signals were found in both gray matter and white matter of the spinal cord in SCI mice treated with BioPAP2 and BioPAP4 (FIGS. 8A, B), especially in the areas of cell bodies and axon cylinders. In contrast, low levels of biotin signals were detected in no-SCI mice treated with BioPAP2 and in SCI mice treated with bioRP compared to no-injury and injury controls, suggesting moderate access of TAT-conjugated PAP2 into non-injured CNS and partial washout of biotinylated RP in SCI mice during animal perfusion and tissue processing. Moreover, the considerable diffusion of Bio-PAP2 and BioPAP4 into the lesioned spinal cord was confirmed by precipitating biotin-conjugated peptides in the lysates of fresh spinal cord tissues (FIG. 8C). Because mice were perfused with cold phosphate buffered saline (PBS) for over 5 min before spinal cord tissue collection, the detected peptide signals should mainly come from the intracellular compartments. Thus, PTEN peptides efficiently penetrated into the lesioned spinal cord following systemic application.

Discussion

PTEN is a critical intra-neuronal factor limiting the regenerative capacities of injured CNS axons. As a general phosphatase inhibitor, bpV targets enzymes other than PTEN and may cause side effects in vivo. A method to suppress PTEN selectively can be a valuable strategy for promoting axon regeneration in the CNS. Novel and selective antagonist peptides for PTEN by targeting its PIP2, ATP-type, PDZ and PDZ-recognizing domains were identified, as disclosed herein. By using different in vitro approaches, the biological activities of PAPs 1-4 were identified, including their efficient binding to PTEN expressed in transfected COS7 cells, promotion on neurite outgrowth and blockade of PTEN downstream signals. Importantly, systemic PAP treatment significantly stimulated growth of descending serotonergic fibers in the distal spinal cord of adult SCI rodents. Additionally, enhanced sprouting of CST axons rostral to the lesion and a limited degree of growth of CST axons in the caudal spinal cord was found. Consistently, PAP treatments significantly enhanced recovery of locomotor function after SCI. Thus, systemically deliverable small peptide compounds to block PTEN selectively were developed and were shown herein to be able to promote regrowth of injured CNS axons following post-injury administration.

Axon Growth in Descending Tracts of Adult SCI Rodents Following Systemic PTEN Peptide Treatments.

A partial injury model was employed due to the experimental difficulties posed by complete spinal transection. In these circumstances, the existence of spared axons can make a determination as to whether an increase in density of anterogradely labeled fibers in the caudal spinal cord represents regeneration of severed axons, sprouts of spared fibers, or both. On the other hand, studies in optic nerve are less ambiguous, even though one could argue that RGCs, like DRGs, are not typical of central neurons.

Following lens injury, cell transplantation and zymosan administration, inflammatory responses have been shown to stimulate significant axon regeneration of different types of neurons, including RGCs and DRG neurons (37, 38). Some cytokines generated by various glial cells, such as oncomodulin, ciliary neurotrophic factor and leukemia inhibitory factor, appear to link inflammation to the improved neuronal growth (38). Intracellularly, the PI3K/Akt/mTOR pathway appears to be essential for regulating axon growth by various cytokines (17). Deletion of PTEN or TSC1 stimulated remarkable growth in injured axons of RGCs and descending CST neurons by activating mTOR (2, 14, 17) a key signal to regulate protein synthesis during cell growth. Thus, PTEN and mTOR are critical signals for controlling growth of mature neurons. Consistently, PTEN blockade with small peptides significantly stimulated growth of descending serotonergic tracts (FIG. 5), which contribute to locomotor recovery after SCI (30). Because dorsal over-hemisection spared a small portion of 5-HT axons in the ventral spinal cord (29, 31), the increased 5-HT fibers detected in the caudal spinal cord in PAP-treated mice could derive from regenerating fibers of lesioned tracts and/or sprouting of spared fibers following PTEN blockade with peptides.

Many groups have reported a limited degree of sprouting or regenerative growth of injured CST axons by inhibiting myelin-associated inhibitors and scar-rich proteoglycans (6, 31), applying neurotrophic factors (39), suppressing intracellular RhoA and GSK-3β signals (25, 40), transplanting grafts or combining different strategies (41-43). In contrast, the He group demonstrated a greater number of regenerative growth of injured CST axons in addition to compensatory sprouting in conditional PTEN knockout mice (16). Thus, the integrity of CST axons was evaluated in mice with a dorsal transection, a model that was used in the He's study (16). Although sprouting of transected CSTs rostral to the lesion was detected, almost all the sprouts terminated before reaching the lesion epicenter and only a limited number of BDA-labeled axons projected into the caudal spinal cord (FIG. 6). Thus, similar to other studies (31), scar tissues round the lesion strongly block regeneration of axotomized CST axons in the PAP-treatment mice. It is less clear how regenerating CST axons crossed scar tissues following PTEN knockdown (1). By using several approaches, high efficiency of the sequence targeting peptides for blocking PTEN signaling pathway have been confirmed. PAPs 1-4 efficiently bound to PTEN protein, blocked its downstream signals and promoted significant neurite extension in adult and postnatal neurons cultured on inhibitory substrates (FIG. 1, 2, 4). To evaluate therapy for patients, PAP treatments were initiated 2 days after axon lesion.

Improved Functional Recovery in SCI Mice Treated with Systemic PAPs.

Systemic PAPs starting two days after SCI significantly enhances growth of descending projecting axons and recovery of locomotor function in adult rodents. PTEN inhibition following PAP treatment is probably the molecular basis for the increased axon growth and improved behavioral recovery in this study. The disclosed peptides selectively bind to PTEN expressed in transfected mammalian cells and efficiently block PTEN activity (FIGS. 2 and 4) due to complete sequence overlap with functional domains of PTEN (Table 1). The biological activity of the disclosed PAPs were confirmed by detecting enhanced neurite growth of cultured neurons, efficient diffusion into injured spinal cord and increased axonal growth in the caudal spinal cord following PAP treatments (FIG. 1, 5-7). In contrast, the previously reported protective and beneficial effects of bpV compounds in SCI rodents might be attributed to inhibition of PTEN as well as other tyrosine phosphatases due to the less selectivity of bpV (20, 21).

After SCI, functional recovery largely depends on the reorganization of segmental circuitry and restoration of supraspinal input. The enhanced supraspinal sprouting and/or regeneration to the caudal spinal cord probably contributed to the functional improvement in PAP-treated mice although segmental mechanisms appeared to play a major role in the locomotor recovery of control SCI mice due to lack of obvious axon regeneration. Systemic PAPs induced axonal growth in the spinal cord below lesion and significantly increased the number of raphespinal 5-HT fibers. A very small number of CST axons were detected in the caudal spinal cord, but the actual regenerating CST fibers might be much greater than that observed because anterograde tracing with BDA only labels a small fraction of total CSTs (44). The increased CST sprouts rostral to the lesion might also contribute to functional recovery through establishment of propriospinal neuronal relays (34). Without being bound to a particular theory, it is likely that the sprouting, regeneration and reorganization of other descending fibers, such as rubrospinal axons, also contribute to the enhanced functional recovery due to widespread expression of PTEN in the CNS (45).

TABLE 1

Summary of the sequence-targeting peptides for PTEN

| Name | Targeting domain: Sequence | Add TAT AA# | MW | Optimal dose (µg/ml) |
|---|---|---|---|---|
| PAP1 | PIP2: MTAIIKEIVSRNKRR (SEQ ID NO: 1) | Yes 26 | 3297 | 2.5 |
| PAP2 | ATP-type B: KHKNHYKIYNLCAE (SEQ ID NO: 2) | Yes 25 | 3243 | 10 |
| PAP3 | ATP-type A: IHCKAGKGRTGVMIC (SEQ ID NO: 3) | Yes 26 | 3056 | 5 |
| PAP4 | C-terminal tail: TVEEPSNPEASSSTSVTPD (SEQ ID NO: 4) | Yes 30 | 3416 | 5 |
| PAP5 | PDZ: PENEPFDEDQHSQITKV (SEQ ID NO: 5) | Yes 28 | 3824 | 5 |

PTEN-blocking peptides may promote recovery also through other mechanisms, such as protecting injured spinal cord tissues, enhancing myelinaton and stimulating proliferation and differentiation of endogenous stem cells. PAP treatments increased the BMS locomotor scores 2-5 weeks after SCI (FIG. 7). Without being bound to a particular theory, the early better recovery might be attributed to neuroprotection and short-range axon sprouting following PTEN suppression. In fact, PTEN deletion protected RGCs from death after optic nerve injury (14). Intrathecal bpV treatment protected long-projecting axons, myelin and blood vessels as well as improved functional recovery in SCI rats (20). Systemic bpV, which elevated the levels of phosphorylated Akt and S6 in the lesioned spinal cord, reduced neuronal death and cavity formation, increased tissue sparing, and improved functional recovery in SCI rats (21). PTEN deficiency resulted in increased myelin thickness and profound and progressive enlargement of most white matter tracts in mice (46). Moreover, PTEN deletion regulated development and proliferation of stem cells or progenitors in the CNS (47).

Therapeutic Potential of PTEN Antagonist Peptides in Patients with CNS Injuries.

Regulating the P13K/PTEN/mTOR pathway pharmacologically is a promising approach for treating patients with CNS injuries. Small PTEN peptides were demonstrated to significantly promote axonal growth and behavioral recovery after CNS injuries in adult mammals. Subcutaneous injections of the disclosed PAPs initiated two days after axonal lesions may provide a basis for achieving effective axon regeneration and locomotor recovery in patients given the wide applications of FDA-approved peptide drugs in humans. Activation of mTOR a few weeks prior to axon injury could stimulate extensive regeneration of CST fibers (16), suggesting that initiating peptide treatment at an earlier time point, such as 2-3 hours after lesion, a time frame also feasible for treating many acutely-injured patients, may achieve a greater extent of axon regeneration and functional recovery. Moreover, the antagonist peptides can be combined with other effective strategies, such as small peptides to block scar-mediated suppression (29), to target multiple mechanisms for neuronal growth failure. Highly invasive therapies have been tested orally in patients with functionally complete SCI (ASIA A) because they have less to lose in case of complications. However, these patients are the least likely to improve, which might discourage extending randomized clinical trials beyond Phase 1 or 2. Development of less invasive and systemically administered therapies can allow regenerative strategies to extend to patients with incomplete SCI, thus greatly increasing patient recruitment and the likelihood of success.

The disclosed subject matter is not to be limited in scope by the specific embodiments described herein. Indeed, various modifications of the disclosed subject matter, in addition to those described herein, will become apparent to those skilled in the art from the foregoing description and the accompanying figures. Such modifications are intended to fall within the scope of the appended claims.

Patents, patent applications and publications are cited throughout this application, the disclosures of which are incorporated herein by reference in their entireties.

REFERENCES

1. Fehlings, M. G., Theodore, N., Harrop, J., Maurais, G., Kuntz, C., Shaffrey, C. I., Kwon, B. K., Chapman, J., Yee, A., Tighe, A., et al. 2011. A phase I/IIa clinical trial of a recombinant Rho protein antagonist in acute spinal cord injury. *J Neurotrauma* 28:787-796.
2. Park, K. K., Liu, K., Hu, Y., Kanter, J. L., and He, Z. 2010. PTEN/mTOR and axon regeneration. *Exp Neurol* 223:45-50.
3. GrandPre, T., Nakamura, F., Vartanian, T., and Strittmatter, S. M. 2000. Identification of the Nogo inhibitor of axon regeneration as a Reticulon protein. *Nature* 403:439-444.
4. Chen, M. S., Huber, A. B., van der Haar, M. E., Frank, M., Schnell, L., Spillmann, A. A.; Christ, F., and Schwab, M. E. 2000. Nogo-A is a myelin-associated neurite outgrowth inhibitor and an antigen for monoclonal antibody IN-1. *Nature* 403:434-439.
5. Jones, L. L., Margolis, R. U., and Tuszynski, M. H. 2003. The chondroitin sulfate proteoglycans neurocan, brevican, phosphacan, and versican are differentially regulated following spinal cord injury. *Exp Neurol* 182:399-411.
6. Bradbury, E. J., Moon., L. D., Popat, R. J., King, V. R., Bennett, G. S., Patel, P. N., Fawcett, J. W., and McMahon, S. B. 2002. Chondroitinase ABC promotes functional recovery after spinal cord injury. *Nature* 416:636-640.
7. Kaneko, S., Iwanami, A., Nakamura, M., Kishino, A., Kikuchi, K., Shibata, S., Okano, H. J., Ikegami, T., Moriya, A., Konishi, O., et al. 2006. A selective Sema3A inhibitor enhances: regenerative responses and functional recovery of the injured spinal cord. *Nat Med* 12:1380-1389.
8. Kantor, D. B., Chivatakarn, O., Peer, K. L., Oster, S. F., Inatani. M., Hansen, M. J., Flanagan, J. G., Yamaguchi, Y., Sretavan, D. W., Giger. R. J., et al. 2004. Semaphorin 5A Is a Bifunctional Axon Guidance Cue Regulated by Heparan and Chondroitin Sulfate Proteoglycans. *Neuron* 44:961-975.
9. Jones, L. L., Oudega, M.; Bunge, M. B., and Tuszynski, M. H. 2001. Neurotrophic factors, cellular bridges and gene therapy for spinal cord injury. *J Physiol* 533:83-89.
10. Busch, S. A., and Silver, J. 2007. The role of extracellular matrix in CNS regeneration. *Curr Opin Neurobiol* 17:120-127.

11. McGee, A. W., and Strittmatter, S. M. 2003. The Nogo-66 receptor: focusing myelin inhibition of axon regeneration. *Trends Neurosci* 26:193-198.
12. Goldberg, J. L., Klassen, M. P., Hua, Y., and Barres, B. A. 2002. Amacrine-signaled loss of intrinsic axon growth ability by retinal ganglion cells. *Science* 296:1860-1864.
13. Gao, Y., Deng, K., Hou, J., Bryson, J. B., Barco, A., Nikulina, E., Spencer, T., Mellado, W., Kandel, E. R., and Filbin, M. T. 2004. Activated CREB is sufficient to overcome inhibitors in myelin and promote spinal axon regeneration in vivo. *Neuron* 44:609-621.
14. Park, K. K., Liu, K., Hu, Y., Smith, P. D., Wang, C., Cai, B., Xu, B., Connolly, L., Kramvis, I., Sahin, M., et al. 2008. Promoting axon regeneration in the adult CNS by modulation of the PTEN/mTOR pathway. *Science* 322: 963-966.
15. Moore, D. L., Blackmore, M. G., Hu, Y., Kaestner, K. H., Bixby, J. L., Lemmon, V. P., and Goldberg, J. L. 2009. KLF family members regulate intrinsic axon regeneration ability. *Science* 326:298-301.
16. Liu, K., Lu, Y., Lee, J. K., Samara, R., Willenberg, R., Sears-Kraxberger, I., Tedeschi, A., Park, K. K., Jin, D., Cai, B., et al. 2010. PTEN deletion enhances the regenerative ability of adult corticospinal neurons. *Nat Neurosci* 13:1075-1081.
17. Sun, F., Park, K. K., Belin, S., Wang, D., Lu, T., Chen, G., Zhang, K., Yeung, C., Feng, G., Yankner, B. A., et al. 2011. Sustained axon regeneration induced by co-deletion of PTEN and SOCS3. *Nature* 480:372-375.
18. Christie, K. J., Webber, C. A., Martinez, J. A., Singh, B., and Zochodne, D. W. 2010. PTEN inhibition to facilitate intrinsic regenerative outgrowth of adult peripheral axons. *J Neurosci* 30:9306-9315.
19. Ning, K., Drepper, C., Valori, C. F., Ahsan, M., Wyles, M., Higginbottom, A., Hermann, T., Shaw, P., Azzouz., M., and Sendtner, M. 2010. PTEN depletion rescues axonal growth defect and improves survival in SMN-deficient motor neorons. *Hum Mol Genet* 19:3159-3168.
20. Nakashima, S., Arnold, S. A, Mahoney, E. T., Sithu, S. D., Zhang, Y. P., D'Souza, S. E., Shields, C. B., and Hagg, T. 2008. Small molecule protein tyrosine phosphatase inhibition as a neuroprotective treatment after spinal cord injury in adult rats. *J Neurosci* 28:7293-7303.
21. Walker, C. L., Walker, M. J., Liu, N. K., Risberg, E. C., Gao, X., Chen, J., and Xu, X. M. 2012. Systemic bisperoxovanadium activates Akt/mTOR, reduces autophagy, and enhances recovery following cervical spinal cord injury, *PLoS One* 7:e30012.
22. Lobo, G. P., Waite. K. A., Planchon, S. M., Romigh, T., Nassif, N. T., and Eng, C. 2009. Germline and somatic cancer-associated mutations in the ATP-binding motifs of PTEN influence its subcellular localization and tumor suppressive function. *Hum Mol Genet* 18:2851-2862.
23. Valiente, M., Andres-Pons, A., Gomar; B., Torres, J., Gil, A., Tapparel, C., Antonarakis, S. E., and Pulido, R. 2005. Binding of PTEN to specific PDZ domains contributes to PTEN protein stability and phosphorylation by microtubule associated serine/threonine kinases. *J Biol Chem* 280:28936 28943.
24. Schwarze, S. R., Ho, A., Vocero Akbani, A., and Dowdy, S. F. 1999. In vivo protein transduction: delivery of a biologically active protein into the mouse. *Science* 285: 1569-1572.
25. Dill, J., Wang, H., Zhou, F. Q., and Li, S. 2008. Inactivation of glycogen synthase kinase-3 promotes axonal growth and recovery in the CNS. *J Neurosci* 28:8914-8928.
26. Gupta, A., and Dey, C. S. 2012. PTEN, a widely known negative regulator of insulin/PI3K signaling, positively regulates neuronal insulin resistance. *Mol Biol Cell* 23:3882-3898.
27. Sayas, C. L., Avila, J., and Wandosell, F. 2002. Glycogen synthase kinase-3 is activated in neuronal cells by Galpha12 and Galpha13 by Rho-independent and Rho-dependent mechanisms. *J Neurosci* 22:6863-6875.
28. Zhou; F. Q., Zhou, J., Dedhar, S., Wu, Y. H., and Snider, W. D. 2004. NGF-induced axon growth is mediated by localized inactivation of GSK-3beta and functions of the microtubule plus end binding protein APC. *Neuron* 42:897-912.
29. Fisher, D., Xing, B., Dill, J., Li, H., Hoang, H. H., Zhao, Z., Yang, X. L., Bachoo, R., Cannon, S., Longo, F. M., et al. 2011. Leukocyte Common Antigen-Related Phosphatase Is a Functional Receptor for Chondroitin Sulfate Proteoglycan Axon Growth Inhibitors. *J Neurosci* 31:14051-14066.
30. Li, S., Liu, B. P., Budel, S., Li, M., Ji, B., Walus, L., Li, W., Jirik, A., Rabacchi, S., Choi, E., et al. 2004. Blockade of Nogo-66, myelin-associated glycoprotein, and oligodendrocyte myelin glycoprotein by soluble Nogo-66 receptor promotes axonal sprouting and recovery after spinal injury. *J Neurosci* 24:10511-10520.
31. Li, S., and Strittmatter, S. M. 2003. Delayed systemic Nogo-66 receptor antagonist promotes recovery from spinal cord injury. *J Neurosci* 23:4219-4227.
32. Weidner, N., Ner, A.; Salimi, N., and Tuszynski, M. H. 2001. Spontaneous corticospinal axonal plasticity and functional recovery after adult central nervous system injury. *Proc Natl Acad Sci USA* 98:3513-3518.
33. Basso, D. M., Fisher, L. C., Anderson, A. J., Jakeman, L. B., McTigue, D. M., and Popovich, P. G. 2006. Basso Mouse Scale tor locomotion detects differences in recovery after spinal cord injury in five common mouse strains. *J Neurotrauma* 23:635-659.
34. Courtine, G., Song, B., Roy, R. R., Zhong, H., Herrmann, J. E., Ao, Y., Qi, J., Edgerton, V. R., and Sofroniew, M. V. 2008. Recovery of supraspinal control of stepping via indirect propriospinal relay connections after spinal cord injury. *Nat Med* 14:69-74.
35. Schnell, L., Fearn, S., Klassen, H., Schwab, M. E., and Perry, V. H. 1999. Acute inflammatory responses to mechanical lesions in the CNS: differences between brain and spinal cord. *Eur J Neurosci* 11:3648-3658.
36. Rapoport, M., and Lorberboum-Galski, H. 2009. TAT-based drug delivery system—new directions in protein delivery for new hopes? *Expert Opin Drug Deliv* 6:453-463.
37. Lu, X., and Richardson, P. M. 1991. Inflammation near the nerve cell body enhances axonal regeneration. *J Neurosci* 11:972-978.
38. Benowitz, L. I., and Popovich, P. G. 2011. Inflammation and axon regeneration. *Curr Opin Neurol* 24:577-583.
39. Schnell, L., Schneider, R., Kolbeck, R., Barde, Y. A., and Schwab, M. E. 1994. Neurotrophin-3 enhances sprouting of corticospinal tract during development and after adult spinal cord lesion. *Nature* 367:170-173.
40. McKerracher, L., and Higuchi, H. 2006. Targeting Rho to stimulate repair after spinal cord injury. *J Neurotrauma* 23:309-317.
41. Li, Y., Field, P. M., and Raisman, G. 1997. Repair of adult rat corticospinal tract by transplants of olfactory ensheathing cells. *Science* 277:2000-2002.
42. Ruitenberg, M. J., Levison, D. B., Lee, S. V., Verhaagen, J., Harvey, A. R., and Plant, G. W. 2005. NT-3 expression from engineered olfactory ensheathing glia promotes spinal sparing and regeneration. *Brain* 128:839-853.
43. 4.3. Diener, P. S., and Bregman, B. S. 1998. Fetal spinal cord transplants support growth of supraspinal and segmental projections after cervical spinal cord hemisection in the neonatal rat. *J Neurosci* 18:779-793.
44. Brosamle, C., and Schwab, M. E. 1997. Cells of origin, course, and termination patterns of the ventral, uncrossed component of the mature rat corticospinal tract. *J Comp Neurol* 386:293-303.
45. Groszer, M., Erickson, R., Scripture-Adams, D. D., Lesche, R, Trumpp, A., Zack, J. A., Komblum, H. I., Liu, X., and Wu, H. 2001. Negative regulation of neural stem/progenitor cell proliferation by the Pten tumor suppressor gene in vivo. *Science* 294:2186-2189.
46. Goebbels, S., Oltrogge, J. H., Kemper, R., Heilmann, I., Bormuth, I., Wolfer, S., Wichert, S. P., Mobius, W., Liu, X., Lappe-Siefke, C., et al. 2010. Elevated phosphatidylinositol 3,4,5-trisphosphate in glia triggers cell-autonomous membrane wrapping and myelination. *J Neurosci* 30:8953-8964.
47. Amiri, A., Cho, W., Zhou, J., Bimbaum, S. G., Sinton, C. M., McKay, R. M., and Parada, L. F. 20.12. Pten deletion in adult hippocampal neural stem/progenitor cells causes cellular abnormalities and alters neurogenesis. *J Neurosci* 32:5880-5890.
48. Fu, Q., Hue, J., and Li, S. 2007. Nonsteroidal anti-inflammatory drugs promote axon regeneration via RhoA inhibition. *J Neurosci* 27:4154-4164.

The invention claimed is:

1. A method for treatment of a spinal cord injury comprising administering to a subject in need of such treatment, a pharmaceutically effective amount of a PTEN antagonist peptide comprising the amino acid sequence set forth in SEQ ID NO:4.

2. The method of claim 1, wherein the PTEN antagonist peptide further comprises the amino acid sequence of SEQ ID NO:6.

3. The method of claim 1, wherein the subject is a human.

4. A pharmaceutical composition comprising a PTEN antagonist peptide comprising the amino acid sequence set forth in SEQ ID NO:4.

5. The pharmaceutical composition of claim 4, wherein the PTEN antagonist peptide further comprises the amino acid sequence of SEQ ID NO:6.

* * * * *

SEQUENCE LISTING

```
<160> NUMBER OF SEQ ID NOS: 6

<210> SEQ ID NO 1
<211> LENGTH: 15
<212> TYPE: PRT
<213> ORGANISM: Homo sapiens

<400> SEQUENCE: 1

Met Thr Ala Ile Ile Lys Glu Ile Val Ser Arg Asn Lys Arg Arg
1               5                   10                  15

<210> SEQ ID NO 2
<211> LENGTH: 14
<212> TYPE: PRT
<213> ORGANISM: Homo sapiens

<400> SEQUENCE: 2

Lys His Lys Asn His Tyr Lys Ile Tyr Asn Leu Cys Ala Glu
1               5                   10

<210> SEQ ID NO 3
<211> LENGTH: 15
<212> TYPE: PRT
<213> ORGANISM: Homo sapiens

<400> SEQUENCE: 3

Ile His Cys Lys Ala Gly Lys Gly Arg Thr Gly Val Met Ile Cys
1               5                   10                  15

<210> SEQ ID NO 4
<211> LENGTH: 19
<212> TYPE: PRT
<213> ORGANISM: Homo sapiens

<400> SEQUENCE: 4

Thr Val Glu Glu Pro Ser Asn Pro Glu Ala Ser Ser Ser Thr Ser Val
1               5                   10                  15

Thr Pro Asp

<210> SEQ ID NO 5
<211> LENGTH: 17
<212> TYPE: PRT
<213> ORGANISM: Homo sapiens

<400> SEQUENCE: 5

Pro Glu Asn Glu Pro Phe Asp Glu Asp Gln His Ser Gln Ile Thr Lys
1               5                   10                  15

Val
```

```
<210> SEQ ID NO 6
<211> LENGTH: 11
<212> TYPE: PRT
<213> ORGANISM: Human immunodeficiency virus

<400> SEQUENCE: 6

Gly Arg Lys Lys Arg Arg Gln Arg Arg Arg Cys
1               5                   10
```